US012575949B2

(12) United States Patent
Richmond et al.

(10) Patent No.: US 12,575,949 B2
(45) Date of Patent: Mar. 17, 2026

(54) PROSTHETIC/ORTHOSIS SPRING LAYER(S) WITH COMPOSITE RIVET(S)

(71) Applicant: Camp Scandinavia AB, Helsingborg (SE)

(72) Inventors: Jack Richmond, Cleveland, TN (US); Christina Engström, Ödåkra (SE); Gunilla Ström, Helsingborg (SE); Nils Hallberg, Åkarp (SE); Patrik Eriksson, Lund (SE); Heinrich Jordan, Ystad (SE); Jeanette Jordan, Ystad (SE); Robert Törnquist, Limhamn (SE)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 18/652,362

(22) Filed: May 1, 2024

(65) Prior Publication Data
US 2024/0398589 A1 Dec. 5, 2024

Related U.S. Application Data

(60) Provisional application No. 63/471,046, filed on Jun. 5, 2023.

(51) Int. Cl.
*A61F 2/66* (2006.01)

(52) U.S. Cl.
CPC .......... *A61F 2/66* (2013.01); *A61F 2002/665* (2013.01); *A61F 2002/6657* (2013.01)

(58) Field of Classification Search
CPC ................ A61F 2/66; A61F 2002/6614; A61F 2002/6621; A61F 2002/6628;
(Continued)

(56) References Cited

U.S. PATENT DOCUMENTS 2,685,813 A * 8/1954 Lampman ......... B29C 66/03241
411/908
4,478,544 A 10/1984 Strand
(Continued)

FOREIGN PATENT DOCUMENTS

DE 4208941 C2 11/2002
DE 102010049257 B4 5/2015
(Continued)

OTHER PUBLICATIONS

Vincent Fortier, Jean-E Brunel and Louis L Lebel, Fastening composite structures using braided thermoplastic composite rivets. Journal of Composite Materials 2020, vol. 54(6) 801-812; (c) The Author(s) 2019; Article reuse guidelines: sagepub.com/journals-permissions; DOI: 10.1177/0021998319867375; journals.sagepub. com/home/jcm; SAGE.
(Continued)

*Primary Examiner* — Christie Bahena
(74) *Attorney, Agent, or Firm* — Neal, Gerber & Eisenberg LLP

(57) ABSTRACT

Composite materials with certain functional or securement parameters are provided herein. Layered composite prosthetic with spring layers and composite rivets are provided. Fiber reinforced layers are grouped into keel, sole plate or other component and these components are configured to provide a spring action for the prosthetic alone or in combination. One or more composite rivets are installed to secure components together.

21 Claims, 18 Drawing Sheets

(58) Field of Classification Search

CPC ...... A61F 2002/6635; A61F 2002/6642; A61F 2002/665; A61F 2002/6657; A61F 2002/6664; A61F 2002/6671; A61F 2002/6678; A61F 2002/6685; A61F 2002/6692; B29C 65/601; B29C 63/0078; F16B 19/04

See application file for complete search history.

(56) References Cited

U.S. PATENT DOCUMENTS

| | | | |
|---|---|---|---|
| 4,687,395 A * | 8/1987 | Berecz | B29C 66/8322 |
| | | | 411/501 |
| 5,037,444 A | 8/1991 | Phillips | |
| 5,181,933 A | 1/1993 | Phillips | |
| 5,314,282 A * | 5/1994 | Murphy | B29C 66/83221 |
| | | | 411/908 |
| 6,053,946 A | 4/2000 | Wilkinson | |
| 6,165,227 A | 12/2000 | Phillips | |
| 6,197,068 B1 | 3/2001 | Christensen | |
| 6,231,618 B1 | 5/2001 | Schall et al. | |
| 6,254,643 B1 | 7/2001 | Phillips | |
| 6,406,500 B1 | 6/2002 | Phillips | |
| D462,767 S | 9/2002 | Meyer et al. | |
| D462,768 S | 9/2002 | Meyer et al. | |
| 6,514,293 B1 | 2/2003 | Jang et al. | |
| 6,527,811 B1 | 3/2003 | Phillips | |
| 6,562,075 B2 | 5/2003 | Townsend et al. | |
| 6,793,683 B1 | 9/2004 | Laghi | |
| 6,805,717 B2 | 10/2004 | Christensen | |
| 6,929,665 B2 | 8/2005 | Christensen | |
| 7,226,485 B2 | 6/2007 | Townsend et al. | |
| D579,115 S | 10/2008 | Rubie et al. | |
| 7,572,299 B2 | 8/2009 | Christensen | |
| D633,618 S | 3/2011 | Johnson et al. | |
| 8,025,699 B2 | 9/2011 | Lecomte et al. | |
| D653,759 S | 2/2012 | Smith et al. | |
| D655,009 S | 2/2012 | L'Heureux et al. | |
| 8,236,062 B2 | 8/2012 | Townsend et al. | |
| 8,486,156 B2 | 7/2013 | Jónsson | |
| 8,540,781 B2 | 9/2013 | Nissels et al. | |
| D714,939 S | 10/2014 | Gunnsteinsson et al. | |
| D718,861 S | 12/2014 | Halldorsson | |
| 9,011,554 B2 | 4/2015 | Rubie et al. | |
| D731,062 S | 6/2015 | Meyer et al. | |
| D733,884 S | 7/2015 | Hillman et al. | |
| 9,114,029 B2 | 8/2015 | Ásgeirsson et al. | |
| 9,132,022 B2 | 9/2015 | Lecomte et al. | |
| 9,393,132 B2 | 7/2016 | Kranner et al. | |
| D765,849 S | 9/2016 | Radzinsky | |
| D782,679 S | 3/2017 | Taszreak et al. | |
| 9,687,365 B2 | 6/2017 | Ásgeirsson et al. | |
| D797,292 S | 9/2017 | Clausen et al. | |
| 10,034,782 B2 | 7/2018 | Sandahl | |
| 10,624,765 B2 | 4/2020 | Sandahl | |
| 10,646,357 B2 | 5/2020 | Boiten et al. | |
| 10,695,198 B2 | 6/2020 | Jonasson et al. | |
| 10,881,534 B2 | 1/2021 | Fairley et al. | |
| D915,596 S | 4/2021 | Gunnarsson et al. | |
| 11,026,814 B2 | 6/2021 | Klute et al. | |
| 11,607,325 B2 | 3/2023 | Winter et al. | |
| 11,730,610 B2 | 8/2023 | Breuninger et al. | |
| 2003/0144745 A1 | 7/2003 | Phillips | |
| 2003/0191541 A1 | 10/2003 | Phillips | |
| 2005/0038524 A1* | 2/2005 | Jonsson | A61F 2/66 |
| | | | 623/55 |
| 2012/0179274 A1 | 7/2012 | Christensen | |
| 2013/0267878 A1 | 10/2013 | Franke et al. | |
| 2014/0046456 A1 | 2/2014 | Smith et al. | |
| 2014/0156027 A1 | 6/2014 | Smith et al. | |
| 2015/0088270 A1 | 3/2015 | Doddroe et al. | |
| 2015/0374514 A1* | 12/2015 | Clausen | A61F 2/66 |
| | | | 623/53 |
| 2016/0038311 A1 | 2/2016 | Gonzalez et al. | |
| 2016/0100960 A1 | 4/2016 | Smith et al. | |
| 2016/0287411 A1 | 10/2016 | Lindhe et al. | |
| 2018/0263792 A1 | 9/2018 | Lindhe et al. | |
| 2019/0070426 A1 | 3/2019 | Alam | |
| 2019/0125552 A1 | 5/2019 | Day et al. | |
| 2020/0085595 A1 | 3/2020 | Winter et al. | |
| 2020/0085597 A1 | 3/2020 | Green et al. | |
| 2020/0281746 A1 | 9/2020 | Sandahl | |
| 2020/0289294 A1 | 9/2020 | Jonasson et al. | |
| 2020/0375763 A1 | 12/2020 | Winter et al. | |
| 2021/0068989 A1 | 3/2021 | Brenninger et al. | |
| 2021/0307937 A1 | 10/2021 | Parker et al. | |
| 2022/0079781 A1 | 3/2022 | Clausen et al. | |
| 2023/0064710 A1 | 3/2023 | Ossur | |
| 2023/0201008 A1 | 6/2023 | Pusch et al. | |
| 2023/0301804 A1 | 9/2023 | Mönicke et al. | |
| 2024/0207071 A1 | 6/2024 | Pohl et al. | |

FOREIGN PATENT DOCUMENTS

| | | |
|---|---|---|
| DE | 202015007994 U1 | 12/2016 |
| DE | 102019135178 A1 | 6/2021 |
| DE | 102019135179 A1 | 6/2021 |
| DE | 202020001086 U1 | 7/2021 |
| DE | 202020005719 U1 | 4/2022 |
| DE | 402022100781-0003 | 1/2023 |
| DE | 402022100781-0004 | 1/2023 |
| DE | 402022100781-0005 | 1/2023 |
| DE | 402022100781-0006 | 1/2023 |
| DE | 402022100781-0007 | 1/2023 |
| DE | 402022100781-0008 | 1/2023 |
| EM | 000495882-0001 | 4/2006 |
| EM | 008415541-0001 | 2/2021 |
| WO | 2020022966 A2 | 1/2020 |
| WO | 2022038481 A1 | 2/2022 |

OTHER PUBLICATIONS

International Search Report/Written Opinion—PCT/US2024/030784—Sep. 13, 2024.

Seattle Skride Foot Installation and User Guide Rev X2, Sep. 1, 2022, pp. 1-4.

Seattle Skride, Pricing, Data Analysis, and Coding Approval Letter, Nov. 2, 2022, pp. 1-2.

Trulife, Seattle Skride, K3/K4 Prosthetic Foot, pp. 1-6.

William Burke, FiveFlute, Fasteners and Bolted Joint Design, pp. 1-27, https://www.fiveflute.com/guide/fasteners-and-bolted-joint-design/.

Return to Engineering News, Rivets vs. Bolts and Screws, ACCU a division of ACCU limited, pp. 1-9, https://accu-components.com/us/p/353-why-choose-rivets-over-screws-or-bolts.

* cited by examiner

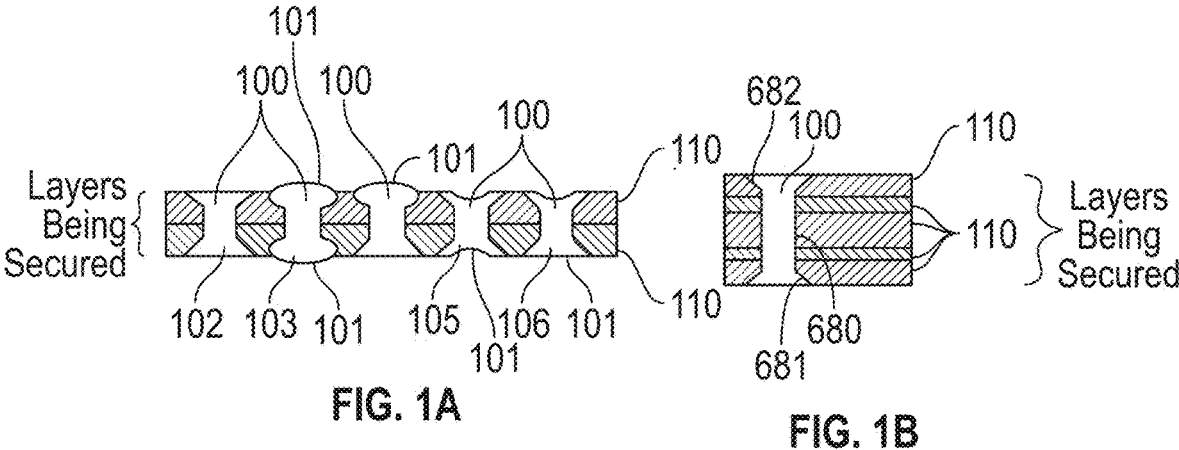
FIG. 1A                    FIG. 1B
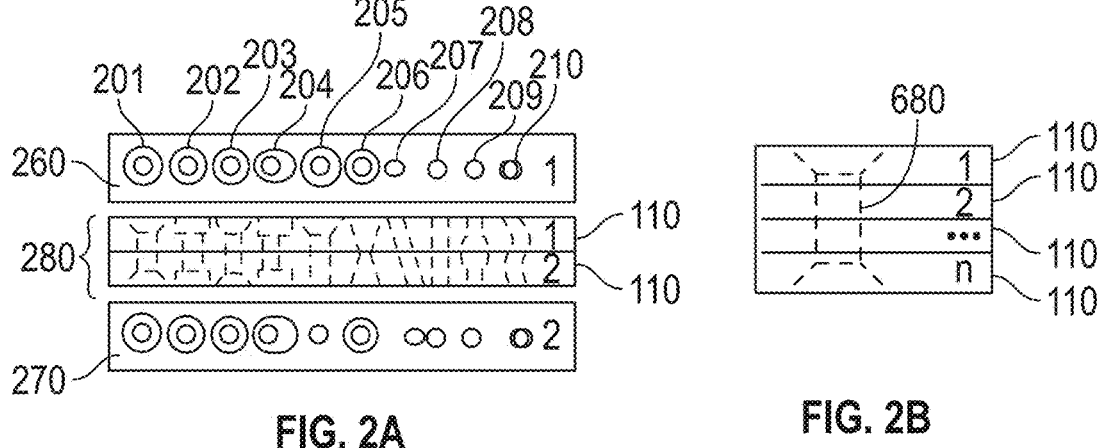
FIG. 2A                    FIG. 2B Rear Perspective View Front Upright View Rear Upright View Side Upright View
With Prosthetic Cover

1445

1310

1340

Side Upright View
With Coupler

Forefoot Rocker

1525

1125

1575

1570

1310

1515

100

680

1/2

1/3

1360

1/3

1/2

1/3

Flexibility Profile

Rigidity Scale = ①to⑤Highest
Lowest

PROSTHETIC/ORTHOSIS SPRING LAYER(S) WITH COMPOSITE RIVET(S)

RELATED APPLICATIONS

This application claims priority to U.S. provisional application 63/471,046, which was filed on Jun. 5, 2023 and is entitled Prosthetic/Orthosis Spring Layer(s) with Composite Rivet(s). The '046 application is incorporated by reference in its entirety herein.

TECHNICAL FIELD

Composite materials with certain functional or securement parameters are provided. Layered composite prosthetic with spring layers and composite rivets are provided.

BACKGROUND

Limb loss is an ongoing problem in the U.S. and around the world. For example, patients who undergo amputation of a lower limb need a prosthetic foot that will allow them to regain their mobility and independence. Patients with lower extremity limb loss or limb difference (LL/LD) are commonly referred to as amputees.

Prosthetics may have various configurations and attachment designs. Prosthetic feet may be manufactured with composite materials including carbon, glass, and/or aramid fiber. These composite elements may be combined with metal components of steel, titanium, and/or aluminum, and/or other materials such as elastomers and plastics. The configuration and placement of these materials, as well as the material's inherent properties, may affect the performance of a prosthetic.

Orthoses may have various configurations as well. They may be employed to provide support of upper or lower limbs during walking, standing, running, holding, etc. Orthoses may be manufactured with composite materials including carbon, glass, and/or aramid fiber. These composite elements may be combined with metal components of steel, titanium, and/or aluminum, and/or other materials such as elastomers and plastics. The configuration and placement of these materials, as well as the materials' inherent properties, may affect the performance of an orthosis.

Embodiments may comprise composite prosthetics or orthoses, configured to perform and provide stability, flexibility, and/or a proper level of energy return. Embodiments may enable patients with limb loss or limb malfunction to ambulate at various speeds throughout their day. Embodiments may employ composite rivets to secure components of various devices together.

FIGURES

FIG. 1A shows a side-sectional view of exemplary composite rivet configurations positioned to secure layers of material together, as may be employed in some embodiments.

FIG. 1B shows a side-sectional view of an exemplary composite rivet positioned to secure layers of material together, as may be employed in some embodiments.

FIG. 2A shows top, bottom, and side-sectional view of passage or hole configurations that may be employed to receive a composite rivet, as may be employed in some embodiments.

FIG. 2B shows a side-sectional view of an exemplary composite rivet passage or hole to secure spring layers of material together, as may be employed in some embodiments.

DETAILED DESCRIPTION

Figure 3A:
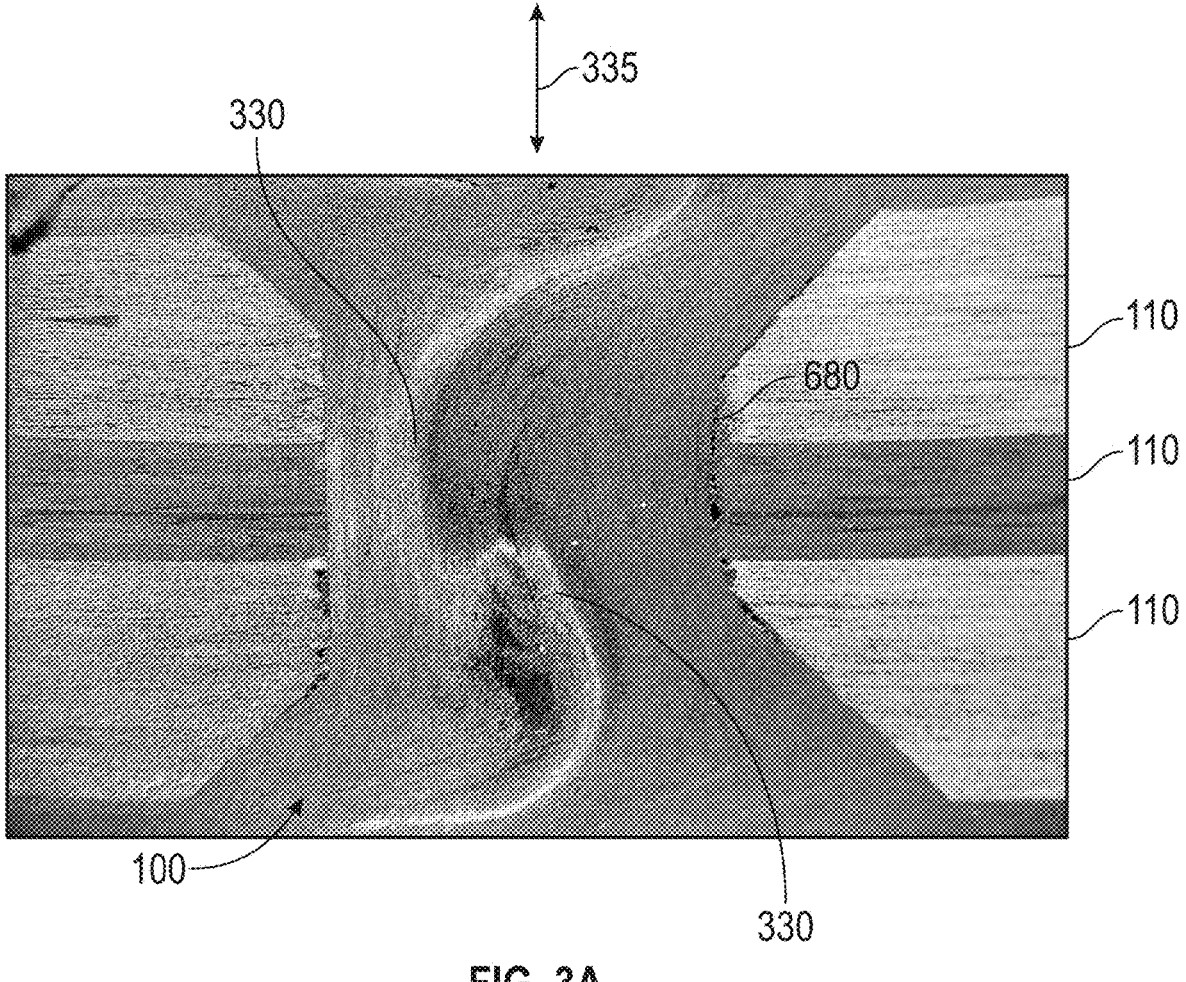
FIGS. 3A-3C show cross-sectional pictures of composite rivets securing layers of a prosthetic together as may be employed in some embodiments.

Prosthetics can be employed as limb replacements for various limbs of the human body. The function and durability of the prosthetic may vary with specific limb replacement and with anticipated uses, as well as with amputation level. For example, prosthetic feet may be tailored to accommodate highly active individuals in some designs and low activity individuals in other designs. Prosthetic feet may fail to provide a desired level of flexibility, stability and energy return due to increased stiffness in key areas of the prosthetic foot. Stiffness of a prosthetic foot may be increased to improve durability and overcome inherent weaknesses of a particular prosthetic foot design. A prosthetic foot of embodiments may be created by different springs. The bottom spring may be called a sole plate or simply a heel, upper springs may be called keels. The numbers and geometry of a sole plate and a keel of embodiments may vary from design to design. Prosthetic foot designs may attach the sole plate to the keel with bolts, windings, and/or glue. However, doing so adds thickness in the toe, which decreases dorsiflexion, and may make such foot designs less stable in late stance and toe off.

Embodiments may comprise prosthetics or orthoses comprising various composite material components. These various composite components may comprise one or more composite rivets to join components of a prosthetic or orthosis. These components being secured may be springs and may comprise single or multiple layers of fiber, some layers may be bidirectional, while other layers may be unidirectional. The fiber may comprise one or more of carbon, aramid, or glass.

In embodiments, composite rivets may be employed to secure components of a prosthetic or orthosis as well as components of other devices. For example, composite rivets may be positioned and sized in prosthetic foot embodiments to allow both the heel and keel of a prosthetic foot to extend to the toe in a continuous flow/motion while minimizing the overall thickness of the prosthetic foot in the forefoot area. This minimizing of thickness may be in comparison designs employing different connection techniques. In some embodiments, springs may be secured to each other with composite rivets. The springs may be layers or other components having spring-like qualities such that they have extended and protracted positions and a propensity to return to a normal, neutral, or unloaded position when not being under a loading condition. Composite rivets may comprise unidirectional or bidirectional fiber layers as well as both.

Embodiments may have other applications in prosthetics and orthoses and other devices as well. For example, composite rivets of embodiments may be employed to join composite prosthetic and/or orthotic static components with a very strong yet small and lightweight fastener. In other words, rigid components, which are intended or designed to remain rigid, thereby, providing support, may be secured to each other with composite rivets in embodiments. Composite rivets may also be employed in other devices as well.

In embodiments, fiber reinforced layers may be grouped into keel, sole plate or other component and these components may be configured to provide a spring action for the prosthetic alone or in combination. One or more composite rivets may be installed to secure components together.

Embodiments may advantageously have a single or primary material composition, for example, carbon fiber laminates. By using a single material composition with different positions, sizes, shapes, etc., performance inequalities derived from designs employing numerous materials, e.g., steel, aluminum, and carbon fiber, may be reduced or eliminated. Multi-material designs can be affected unequally by outside environmental factors as the different materials of the design react differently to outside forces. This variance in material properties and material behaviors can result in different portions of a multi-material prosthetic behaving differently. For example, reactive forces applied to a single-material prosthetic may be less likely to create disproportional reactions when compared to a multi-material prosthetic comprising numerous materials, with each material having different inherent material properties.

Embodiments may employ carbon pre-preg, meaning pre-impregnated carbon fibers. This pre-preg may be employed in various layers of the prosthetics or orthoses or other devices as well as in some or all of the connectors, including the composite rivets described herein. Resins may be employed as the impregnating material of a pre-preg. These resins may be considered an Epoxy and may comprise a thermoset resin.

As used herein, a composite is considered a mix of two or more substances. One of these substances can be fibers that serve as reinforcement. The reinforcement may comprise carbon, glass, and Kevlar, hemp, flax, peck or another type of material that provides reinforcement for another materiel the reinforcement is paired with. Composite may comprise one or more binding materials. Generally, these binding materials may comprise thermoset resin, thermoplastic resin, lactate or even concrete. A thermoplastic resin is fluid or moldable until it cools down. In a thermoset resin heat will change the molecules or bonding and when the resin has cured it cannot go back to previous stage. Often, thermoplastics are thought of as inferior to thermoset resins but this comparison can depend upon the application and the quality of the thermoplastic. A thermoplastic resin can be re-heated and potentially re-shaped.

Embodiments may employ thermoset resins with carbon fiber reinforcement used in unidirectional or multi-directional orientations. Other binding materials and reinforcing materials may be employed in certain embodiments as well.

As noted above, embodiments may employ one or more composite rivet(s), the rivets comprising fiber reinforced materials, for example carbon fiber reinforcements. The composite rivet or rivets may be configured and positioned in a prosthetic or orthotic device or other device. When positioned in a prosthetic or orthotic or other device the rivet may serve to provide suitable or even enhanced binding characteristics to secured sub-components of the prosthetic or orthotic or other device when compared to alternative binding solutions. Composite rivets of embodiments may also provide suitable or enhanced strength for prosthetics or orthotics. These strength characteristics may result in heightened durability of a prosthetic or orthotic or other device in some embodiments. Composite rivets may be employed in various fiber reinforced prosthetics including prosthetics for upper and lower extremities of the human body as well as various upper and lower extremity orthoses. The rivets may be sized to fit within penetrations of the components to be secured together.

In certain embodiments, blanks for the composite rivets may be cut from a sheet of pre-preg where the length, the width and the shape of the blank may be selected to match the anticipated size of the hole and the thickness of the heel and keel or other component(s), to be joined together. Cut single layer and multilayer blanks may be rolled and twisted and introduced to the hole intended to receive the rivet. This hole may be predrilled into one or more components intended to receive the composite rivet. Rolling and twisting of the blanks before, during, or after the insertion of the blank into the hole may serve to equally spread the fibers of the rivet as well as to equally distribute the fibers of the cured rivet. One or more single layer or multilayer blanks may serve as a rivet in embodiments, Once a rivet is inserted, the pre-preg rivets, as well as any components being secured, may be cured by an exothermic reaction. This exothermic reaction may be conducted in an oven under normal atmospheric pressure as well as pressures above atmospheric pressure and below atmospheric pressure.

As to prosthetic designs, embodiments may seek to avoid prosthetic foot designs that stop the sole plate or keel short of the toe and/or eliminate the heel completely. In addition, prosthetic embodiments may seek to avoid foot designs that attach the sole plate to the keel with bolts, filament windings, adhesives, and other methods that introduce a wide area of rigidity into the forefoot. Broad areas of rigidity can serve to reduce the flexibility in the prosthetic forefoot and can have a negative impact on the late stages of gait, in that patient's feel less stable, which leads to abnormal and hence inefficient gait, and possible injury to the patient using such prosthetic designs.

Prosthetic foot embodiments may employ a curved keel. These may include "J" shaped keels, which may have a continuous radius from the attachment point perpendicular to the ground, when in use, and extend to the full-length of the toe. Such "J" shaped keels may also be attached to a sole plate with composite rivets, the rivets being placed where the keel and sole plates meet This joining region may be flat, curved and combinations thereof.

Prosthetic foot embodiments may employ a J-shaped keel design to provide a longer spring lever with flexibility that may replicate ankle plantar and dorsi-flexion. Prosthetic foot embodiments may employ a full-length sole plate that may provide a longer lever to better actuate the J-shaped keel. Prosthetic foot embodiments may employ one or more composite rivets to join elements of the prosthetic foot and thereby allow both the sole and keel to extend to the toe of the prosthetic foot without creating a wide area of rigidity in the forefoot. Other configurations and placements of the composite rivets may be employed in various fiber composite prosthetic embodiments.

Composite rivets of embodiments may employ various constituent materials and various configurations. Unidirectional fiber as well as multi-directional fiber may be employed in composite rivets. These fibers may be carbon, glass, aramid, and other materials as well. The composite rivets may comprise regions of folded layers of fiber as well as regions of twisted fiber layers. The holes (or sometime called passages herein) in which the composite rivets are placed, may have various configurations as well. The holes may have wider outermost areas and more narrow passages therebetween. The outermost areas, e.g., countersunk recesses, may have various configurations including being funnel shaped, U-shaped, and rectangular. Likewise, the passages therebetween may have various configurations including cylindrical, rectangular, and obround. An angle of countersinking of the outermost areas may have countersinking angles in a range of 120°-35° or more or less. In some embodiments, outermost or wider parts, e.g., countersunk recessed, when filled with fiber and binding/matrix may act as the head of a rivet. The head of the rivet may serve to create a mechanical lock providing additional axial compressive strength so that the strength of the joint may not rely solely on frictional adhesion in the cylindrical part of the hole/rivet interface. The outermost areas may have different configurations above and below the shared passage as well as vary from adjacent or nearby holes as well.

As noted above, constituent materials of composite rivets may comprise various materials and/or material combinations. These materials may comprise: UD fiber, rolled UD fiber bunches, weaved fiber stockings, UD fiber bunches, twisted UD fiber bunches, twisted fibers, and roped out fibers. In embodiments the fiber direction may coincide with the length axis of the rod. The matrix can be thermoset or thermoplastic in some embodiments.

Other geometries and positions of the rivet passages and rivets may be employed in embodiments. For example, in embodiments, in addition to or in lieu of composite rivets, looped strands of composite threaded through two adjacent passages may be employed. These strands may reside within a groove between the two passages where the composite strand may lay, thereby giving an overall relatively flat surface and composite strand strength via the passages and strands passing therethrough. Various passage geometries and configurations are shown in FIG. 2A. Other configurations and geometries may also be employed in some embodiments.

Various configurations of prosthetics and orthotics shape and features may be employed in embodiments. Exemplary shapes and features are taught herein, and some may be seen in the accompanying figures. Certain prosthetic embodiment configurations may be adjusted to accommodate for P-levels (force specifications as described by ISO standard 22675: 2016 that are a function of patient weight and activity level). For example, a curve of the surface opposite the build/tooling-surface may be modified to accommodate P-levels, which may result in increasing or decreasing the thickness of the prosthetic composite structure.

Some embodiments may comprise two springs secured with one or more composite rivets. These features may be employed in orthoses as well as prosthetics of embodiments. Some prosthetic embodiments may comprise one or more of the following features: a metallic pyramid coupler at the top of the prosthesis; a metallic coupler cantilevering over the posterior section of the keel; a metallic coupler cantilevering over the posterior section about 25% to 33% of the total foot length; a split heel with split lateral and medial sides for the entire length of the sole plate and no intervening connecting portions; a J-shaped prosthetic where the keel and the sole plate may be attached in the forward ⅓; a J-shaped prosthetic where sole plate and keel may be attached with any of the following: rivets, flexible adhesive, bolts, screws, and rigid adhesive; a J-shaped prosthetic having the keel and sole plate portion attached in their forward ⅓; a heel section of a J-shaped prosthetic that meets the keel behind in the forward ½ of the overall foot length and then returns to neutral position at midstance of a gait cycle; a J-shaped prosthetic where the upright portions of the J have different widths; and a J-shaped prosthetic were the foot portion and upper cantilevered portion of the J may be approximately horizontal when a wearer is standing.

Embodiments may provide, during the late stance of the gait cycle, improved stability, and improved loading of the keel. In embodiments, a broader base of support may be provided to the forefoot at or near toe off in the gait cycle. The flexibility within the composite layup and the smooth surface of the soleplate, from the minimization or absence of connectors in the forefoot, may each contribute to this broader base of support and the dynamic gait benefits.

Exemplary sizing and configurations may be as shown in the accompanying figures Other sizing and configurations may also be employed in some embodiments.

FIG. 1A shows cross sections of composite rivets 100. The rivets 100 are shown extending through at least two layers of material 110, which may be springs known as keel and sole plate. The material 110 may be various types of composites but may also comprise one or more non-composites. The rivets 100 may provide a mechanical connection between the layers of material 110. Also visible in FIG. 1A are that the rivet heads 101 may have various configurations. These may include rounded and flat heads that protrude out of the spring layer or even with the spring layer. Concave, convex, flat, conical, spherical, etc., rivet heads may be employed in some embodiments. In some embodiments, the rivet head 101 may even be recessed from the spring layer or other components being secured. In each of the rivets shown in FIG. 1A the rivet has two opposing heads. These heads may act to help retain the layers being joined together. This reaction may be oriented along a lengthwise axis of the rivets. Indeed, in some embodiments, the heads may act to place compressive force inward along its longitudinal axis such that the layers being secured are squeezed together by the rivet. In embodiments, where one or more composite rivet is present without a head on an upper and/or lower surface, the purpose of the composite rivet may be to secure members from rotation or provide frictional resistance to separation of layers or for both or for other reasons as well.

As is shown in FIG. 1A the rivets 100 may have different head configurations 102, 103, 105, 106 for the same rivet and these head configurations may include chamfered slopes, vertical countersinks, and other passage configurations. In embodiments, the configuration of the rivet may be selected to accommodate the compressive or securement forces needed. The passage's configuration may be selected for the same reason. In some embodiments the shape of the rivet and the shape of the passage may mimic each other. In some embodiments, the passage may be slightly larger than the rivet in its final installed shape while in other embodiments the passage may be slightly narrower than the rivet in its final installed shape. The material layers in FIG. 1A and in other embodiments may vary in thickness and other variations to rivet size, shape, position, layer thickness, etc. may also be employed in embodiments.

FIG. 1A also provides information about securement functionality of rivets. Rivets with a head larger than its column, such as rivet head configurations 102, 103, 105, and 106 can provide axial compressive forces or axial resistance to keep layers of material 110 or other components held together. Where counter sunk holes are present, such as in the rivets 105 and 106 of FIG. 1A, the presence of the rivet in the countersunk area of the hole may also provide some axial resistance to separation of the layers via the recessed heads of these rivets. Comparatively, a rivet may not employ a head and may occupy a straight passage 208 as is shown in FIG. 2A. In these instances, without a countersink passage or rivet with a head, frictional forces between the walls of the passage and the surface of the rivet may provide the sole frictional surface resistance to sheer, separation, rotation or other forces acting on the component rivet connection.

FIG. 1B shows a side-sectional view of an exemplary composite rivet 100 positioned to secure layers of material 110 together, as may be employed in embodiments. Thus, a cross section of a composite rivet extending through several layers of springs is shown and the spring layers may vary in thickness in this and other embodiments. While the passage 680 is shown as a cylinder with top 682 and bottom 681 conical ends various other configurations may be employed in embodiments. The configuration of the top and bottom of the passage may be set so as to provide a constrictive force by the rivet onto the layers being secured together. In other words, if the rivet shrinks in length, this reduction in length may cause a contractive force to be placed by the rivet onto the outermost layers via the conical ends of the passage, which may in turn then also compress the inner layers. Thus, embodiments may employ rivet and passage configurations that serve to apply restrictive forces both through friction at the edges and also through forces developed by rivet contraction or other rivet or passage movement.

Walls or other surfaces of the passages may be treated by grinding, washing or some type of sizing/primer in embodiments. The passages in embodiments may be drilled through multiple layers at once as well as drilled through layers or other components before the components are brought together for joining by a rivet or rivets. Techniques other than drilling may be employed to create the passages through single and multiple layers.

FIGS. 2A and 2B show examples of the passages 201-210 that are made in the layers of material to make room for the composite rivet. FIG. 2A shows top 260, bottom 270, and side-sectional view 280 of passage configurations that may be employed to receive a composite rivet, as may be employed in some embodiments. Thus, examples of the passages that are made in the springs to make room for the composite rivet(s) are shown in FIG. 2A. As can be seen in FIG. 2A, central passages may have various upper and lower opening configurations. These upper and lower openings may be symmetrical, non-symmetrical, centered on each other and the passage, off centered from each other and/or the passage of which they are a part. The passage may be vertical as well as angled and may have distinct portions along its height. The passage may be straight as well as curved as well. Still other configurations of the passages and the upper and lower openings may be employed in embodiments.

FIG. 2B shows a side-sectional view of an exemplary composite rivet passage 680 to secure layers of material together, as may be employed in some embodiments. In this view, four layers 110 are shown, but other layer numbers may be employed. Also, various passage configurations, like those in FIG. 2A or still others may be employed.

Figure 3B:
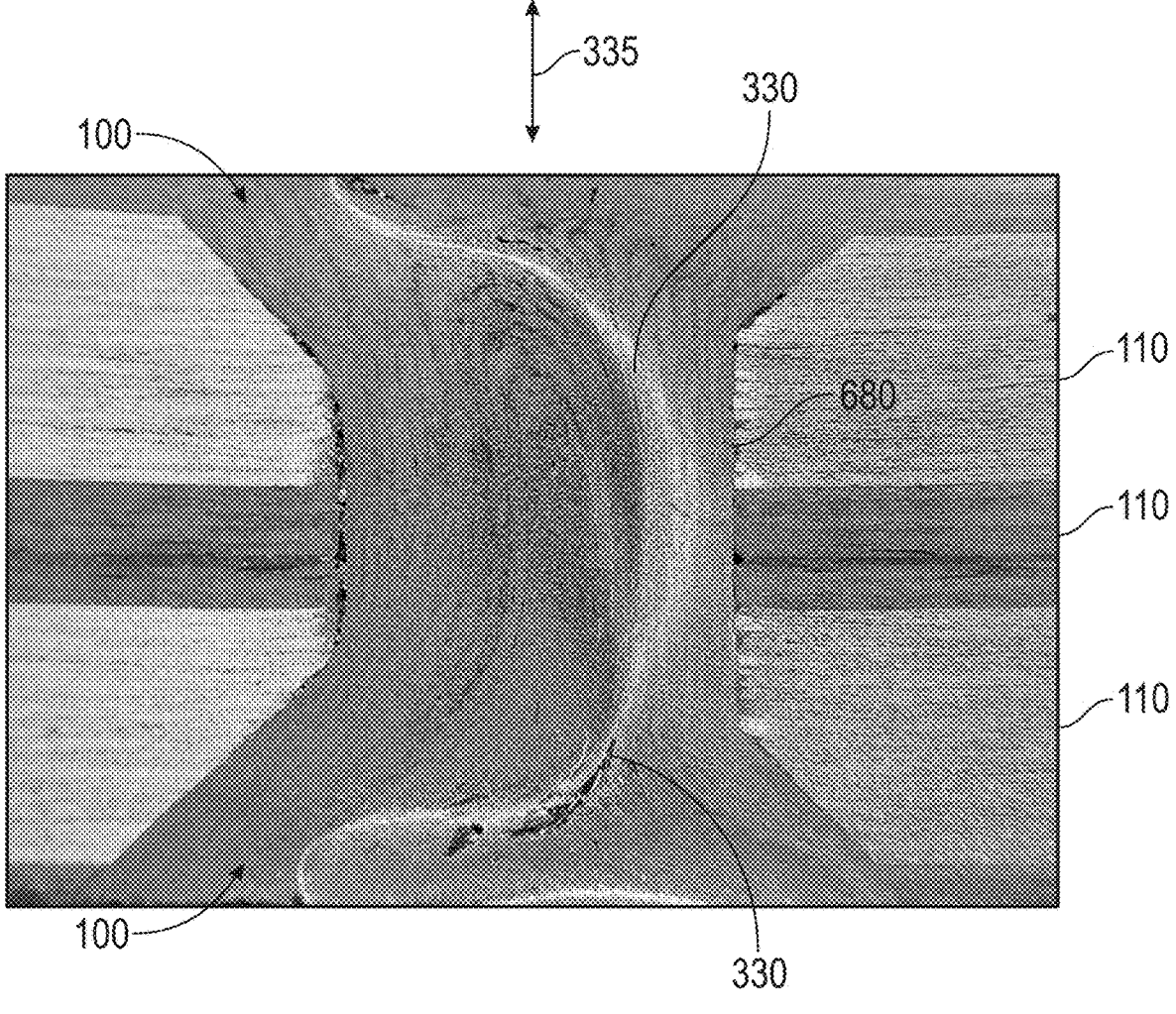
Figure 3C:
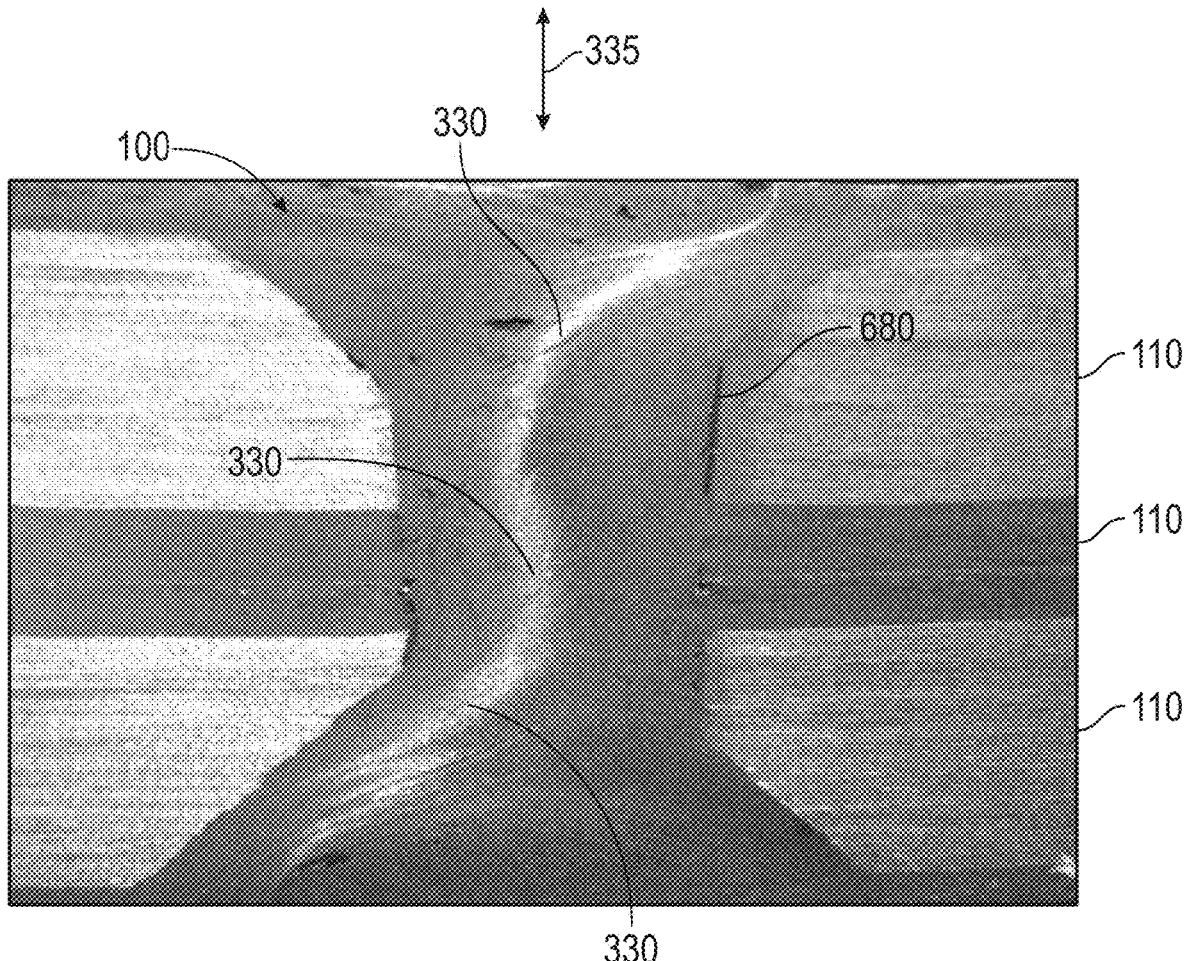

FIGS. 3A-3C show cross-sectional views of composite rivets 100 as may be employed in embodiments. As can be seen, layers of material 110 are being secured together by rivets 100 located in a passage 680 through the materials. Twists 330 in these composite rivets 100, as may be employed in embodiments, are shown in each of FIGS. 3A-3C. These twists 330 may have various configurations when employed as can be seen FIGS. 3A-3C. The twists 330 may comprise a single rotation of the rivet material before insertion as well as a half-turn and multiple turns of the rivet material before insertion in some embodiments. Tight matching between the rivet and the materials to be secured, with little if any spacing therebetween and substantial surface interface between the rivet and the inner surface of the passages, can be seen in FIGS. 3A-3C. Reference line 335 is shown in each of FIGS. 3A-3C.

Figure 4:
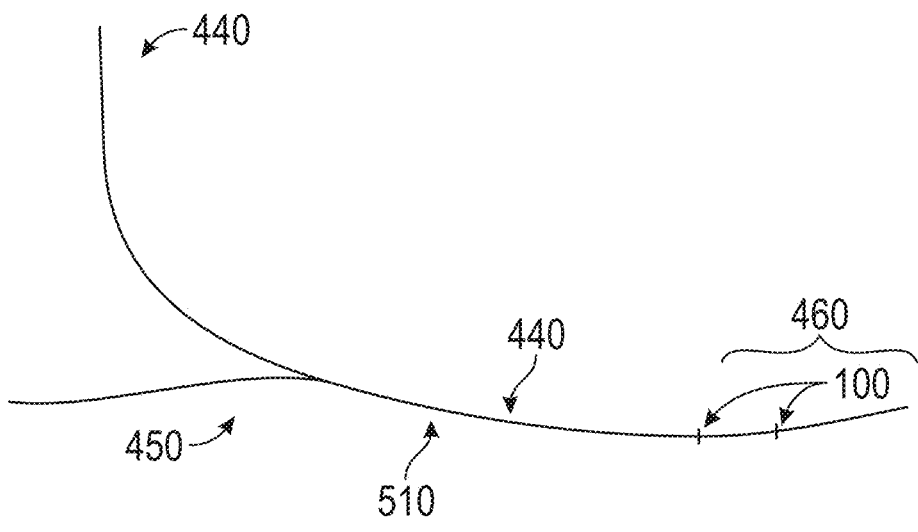
FIG. 4 shows a side view of an L-shaped keel and sole plate, either or both acting as a spring layer, and each secured to the other with composite rivets, as may be employed in some embodiments.

FIG. 4 shows a side view of an L-shaped keel 440 and sole plate 450, either or both acting as a spring layer, and each secured to the other with composite rivets 100, as may be employed in embodiments. In FIG. 4 a view of a basic prosthetic device that may utilize at least one composite rivet for joining springs of composite layers 510 is seen. The keel 440 may employ spring functionality and the sole plate 450 may employ spring functionality and each may be joined by a composite rivet(s) through a passage as taught herein. The composite rivets 100 may serve to secure the two springs together. The composite rivet(s) may be located at various locations of the device. In this instance, the rivets 100 are located in the toe region of the prosthetic 460. During use, the two springs may come apart from each other and then contact back again during a gait cycle while the portions of the two springs may be securely held by the composite rivet 100. The areas joined by the rivet may not separate from each other (or may marginally separate) during the gait cycle while areas nearby the composite rivet may become somewhat separated from each other due to the spring like functionality of the keel spring and the sole plate spring.

Figure 5:
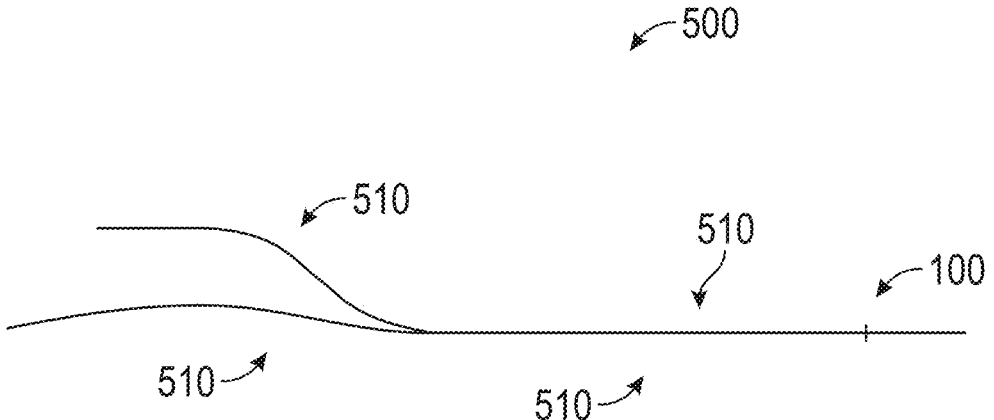
FIG. 5 shows a side view of a low-profile embodiment with composite layers, one or more acting as a spring layer, and all secured to each the other with a composite rivet, as may be employed in some embodiments.

FIG. 5 shows a side view of composite layers 510, one or more acting as a spring layer, and all secured to each the other with a composite rivet 100, as may be employed in embodiments. In FIG. 5, a view of a basic low profile prosthetic device 500 that may utilize at least one composite rivet 100 for joining springs is seen. The upper spring layer may employ spring functionality and the lower spring layer may employ spring functionality and each may be joined by a composite rivet 100 through a passage as taught herein. The composite rivet 100 may serve to secure the two springs 510 together. Composite rivet(s) may be located at various locations of the low-profile device. In this instance the rivet is located in the front third of the device. During use, the two springs 510 may come apart from each other and then contact back again during a loading cycle while the portions of the two springs 510 may be securely held by the composite rivet. The areas joined by the rivet 100 may not separate from each other (or may marginally separate) during the loading cycle while areas nearby the composite rivet may become somewhat separated from each other due to the spring like functionality of the two layers.

Figure 6:
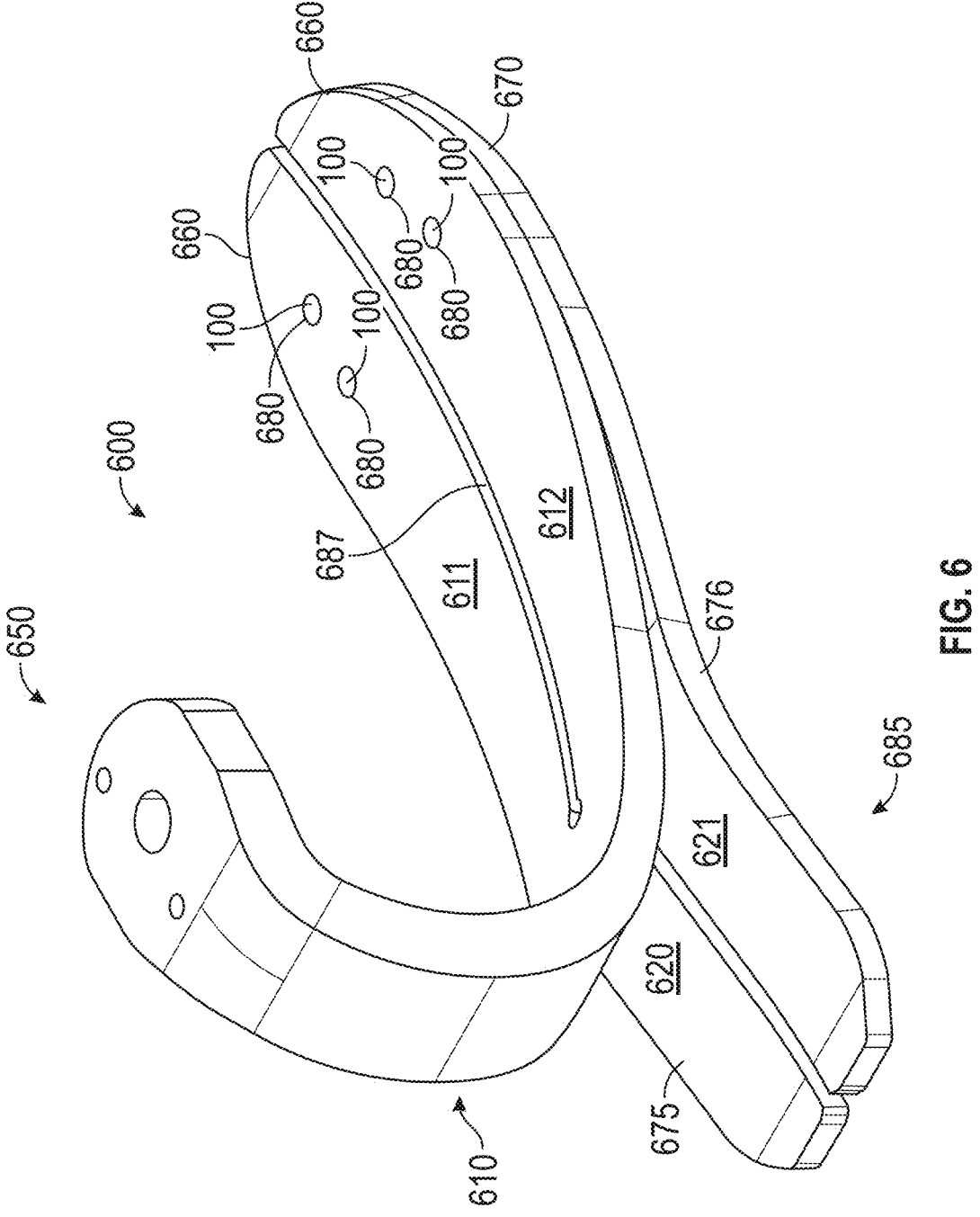
FIG. 6 shows a rear perspective view of a prosthetic foot with split J-shaped keel, multiple sole plates, and composite rivet passages, as may be employed in some embodiments.

FIG. 6 shows a rear perspective view of a prosthetic foot 600 with split J-shaped keel 610 and multiple sole plates 620, 621, as may be employed in embodiments. As can be seen, medial and lateral sole plates 620, 621 are connected to a split J-shaped keel 610 in the prosthetic of FIG. 6. The sole plates 620, 621 and J-shaped keel 610 are coupled in the first third of the prosthetic at the keel toe region 660. The attachment may be done with various techniques, including rivets, flexible adhesive, bolts, screws, thread, composite rivets, and rigid adhesive, among other things. Four passages 680 are present in the region 660 of the prosthetic 600 these passages are shown with rivets 100. These passages may have various configurations, including one or more of geometries taught above in FIG. 2A. The passages may be uniformly and nonuniformly spaced and may have matching or discordant numbers on either side of the split, e.g., two passages on one side and three passages on the other. A top portion 650 of the J-shaped keel 610 may be cantilevered over other portions of the J-shaped keel as well as cantilevered over portions of one or more sole plates. In FIG. 6, two sole plates 620, 621 are shown with each being attached to the J-shaped keel 610 and each running the length of the prosthetic 600. The J-shaped keel 610 is shown with a split 687 running from below the cantilevered upper portion though the keel toe region 660 and between keel prong portions 611, 612. Thus, embodiments may comprise dual sole plates coupled to a single upper J-shaped keel, the dual sole plates extending for most or all of the length of the prosthetic. These sole plates may mimic each other in shape, functionality, etc. or may be different from each other in embodiments. Adjacent sole plates may have identical or different cross-sections. Adjacent sole plates that mimic each other, e.g., have identical or substantially similar cross-sections and material constructions, may exhibit similar or identical properties during use of the prosthetic. Comparatively, adjacent sole plates having different cross-sections, shapes, length, etc., may exhibit different properties during use of the prosthetic. Having different properties/reactions being exhibited during gait or at other times may be helpful to accommodate a patient's needs, for certain other anatomical reasons, or for other reasons as well. Labeled in FIG. 6 are upper cantilevered portion 650, keel 610, sole plate 621, heel region 676, sole plate 620, heel region 675, heel 685, keel prong portions 611, 612, and sole plate 621 toe region 670.

Figure 7:
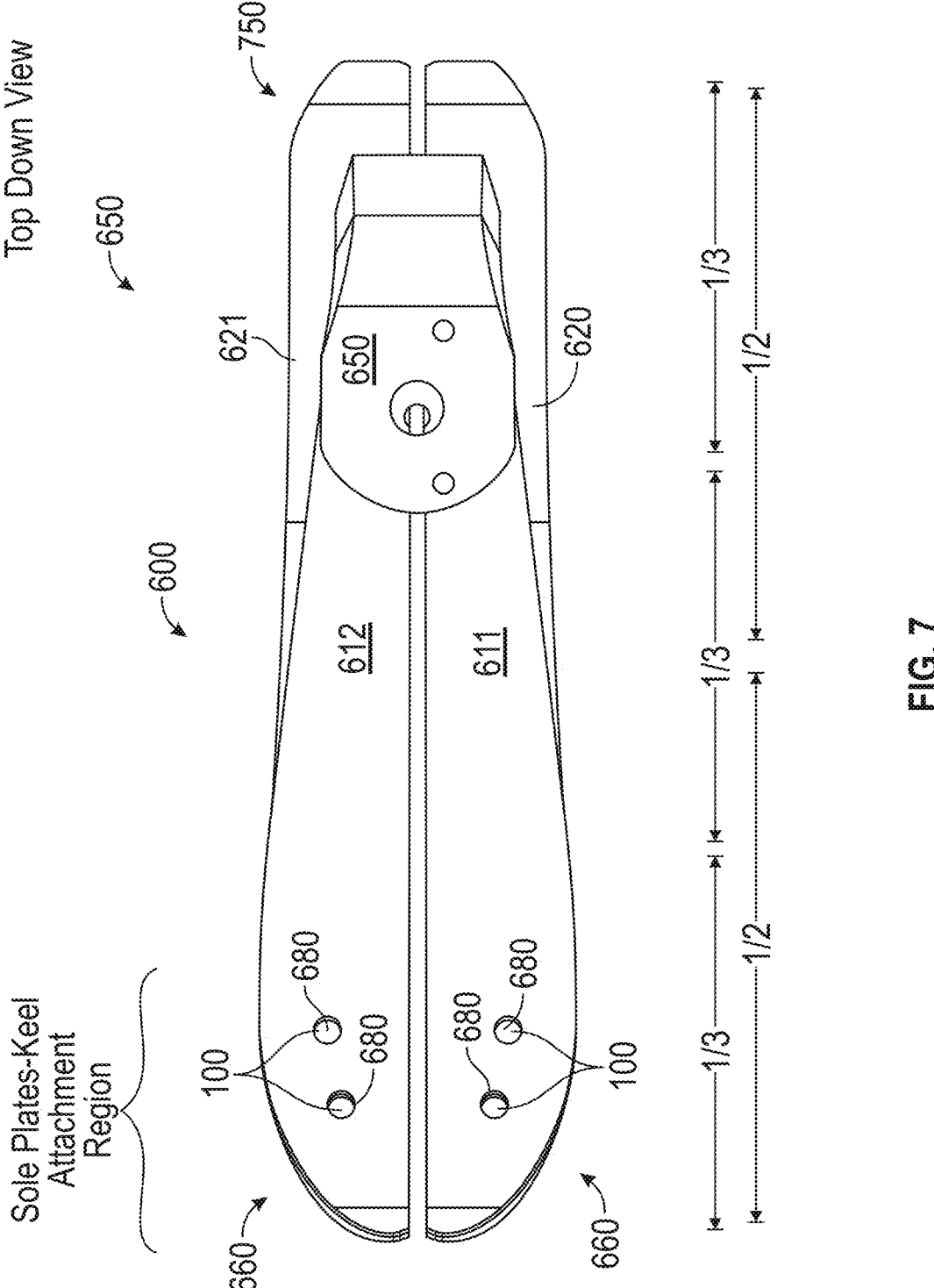
FIG. 7 shows a top-down view of the prosthetic foot of FIG. 6 with split J-shaped keel, multiple sole plates, and composite rivet passages, as may be employed in some embodiments.

FIG. 7 shows a top-down view of the prosthetic foot 600 of FIG. 6 with split J-shaped keel 610 and multiple sole plates 620 and 621 as may be employed in embodiments. A scale is shown near the bottom of FIG. 7. This scale has one-half and one-third markers that can be used to understand the relative positions of various features of the prosthetic of FIG. 6 and of FIG. 7 and of other embodiments being taught herein as well. As can be seen in FIG. 7, the passages 680 at the keel toc region 660 of the prosthetic are positioned in the toe third of the prosthetic while the upper cantilevered portion 650 is shown to be positioned in the heel half of the prosthetic 600. The relative positions of passages 680 in a prosthetic are visible in FIG. 7. As can be seen passages 680 may not be evenly spaced between each other and corresponding holes on an opposite side of a split of the prosthetic foot 600.

Figure 8:
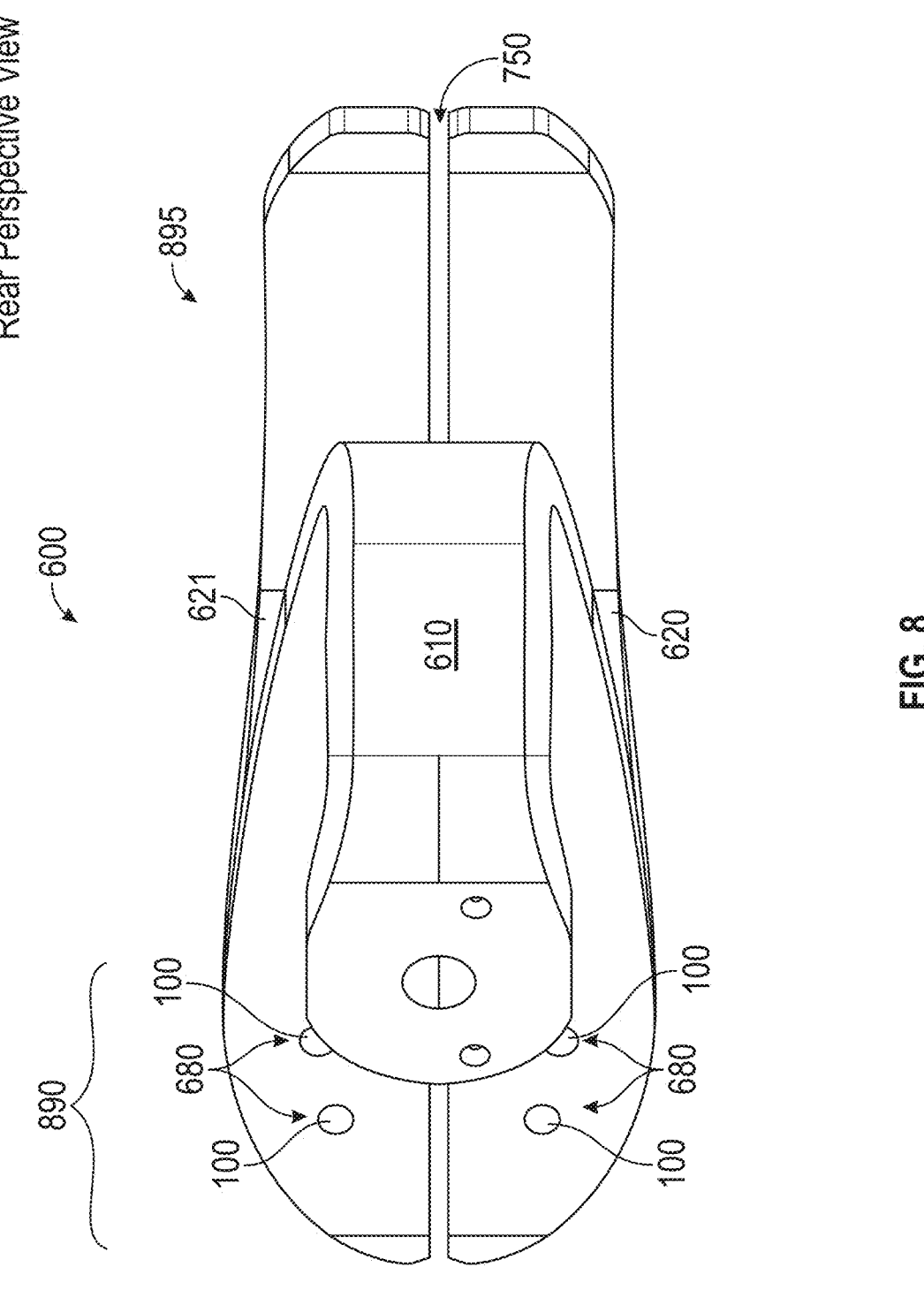
FIG. 8 shows a rear top-down view of the prosthetic of FIG. 6, as may be employed in some embodiments.

FIG. 8 shows a rear perspective view of a prosthetic foot 600 with split J-shaped keel 610 multiple sole plates (labelled 672 and 673 in FIG. 9), and composite rivet passages 680, as may be employed in some embodiments. As can be seen, medial and lateral sole plates 621, 620 are connected to a split J-shaped keel in the prosthetic of FIG. 8. The sole plates and J-shaped keel are coupled in the first third of the prosthetic at the toe end, e.g. a sole plate-keel attachment region. The sole plates-keel attachment region is labelled as 890 in FIG. 8 and the split heel is labelled as 750. The attachment may be done with various techniques, including rivets, flexible adhesive, bolts, screws, thread, composite rivets, and rigid adhesive, among other things. Four passages are present in the toe region of the prosthetic. These passages may have various configurations, including one or more of the passage geometries shown in FIG. 2A. The passages may be uniformly and nonuniformly spaced and may have matching or discordant numbers on either side of the split, e.g., two holes on one side and three holes on the other. A top portion of the J-shaped keel may be cantilevered over other portions of the J-shaped keel as well as cantilevered over portions of one or more sole plates. In FIG. 8, two sole plates are shown with each being attached to the J-shaped keel and each running the length of the prosthetic. The J-shaped keel is shown with a split running from below the cantilevered upper portion though the toe region. Thus, embodiments may comprise dual sole plates coupled to a single upper J-shaped keel, the dual sole plates extending for most or all of the length of the prosthetic. These sole plates may mimic each other or may be different from each other in embodiments. Adjacent sole plates may have identical or different cross-sections. Adjacent sole plates that mimic each other, e.g., have identical or substantially similar cross-sections and material constructions, may exhibit similar or identical properties during use of the prosthetic. Comparatively, adjacent sole plates having different cross-sections, shapes, length, etc., may exhibit different properties during use of the prosthetic. Having different properties/reactions being exhibited during gait or at other times may be helpful to accommodate a patient's needs, for certain other anatomical reasons, or for other reasons as well. The configuration of the ends of the heel portions 895 of the prosthetic foot as well as the uniform spacing between the sole plates are each visible in this view. While a uniform split spacing is shown, embodiments may have various spacing configurations including even spacings, uneven spacings, tapered spacings, and alternating spacings along the length of the split between sole plates of embodiments.

Figure 9:
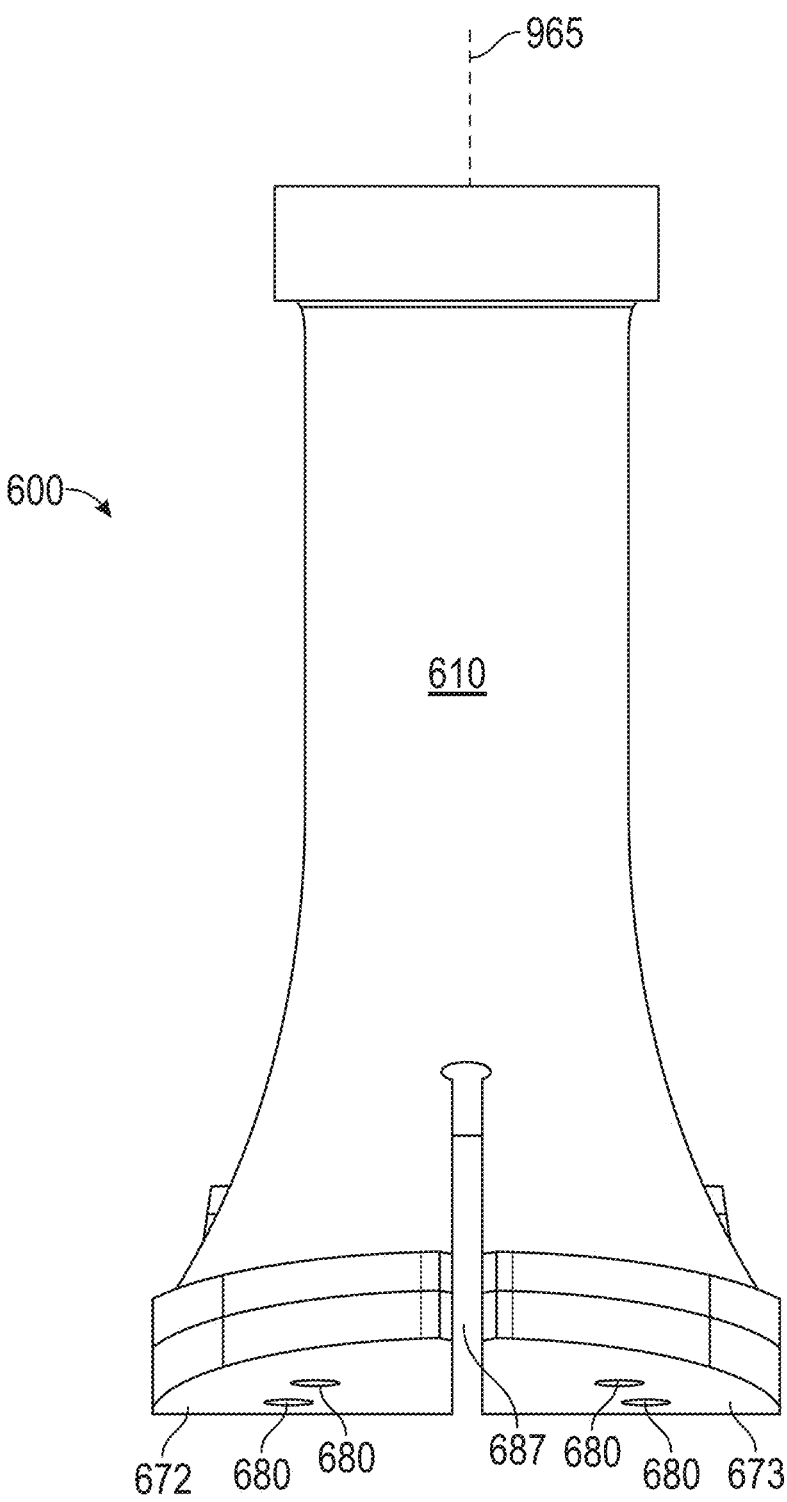
FIG. 9 shows a front upright view, of the prosthetic foot of FIG. 6 with J-shaped keel, passages for composite rivets, and sole plates, as may be employed in some embodiments.

FIG. 9 shows a front upright view, of the prosthetic foot 600 of FIG. 6 with J-shaped keel 610, passages 680 for composite rivets, and sole plates with split between them, as may be employed in some embodiments. Split sole plate 1 is labelled 672 and split sole plate 2 is labelled 673. A prong portion of the J-shaped keel 610 is labelled 611 and another prong portion of the J-shaped keel is labelled 612. The split 687 runs between lateral and medial sides for the entire length of the sole plates without intervening connection points in the prosthetic 600. The location of the underside of the sole plates and the passages 680 of the toe region are visible in this view. Rivets are present in the passages 680 of the prosthetic. As can also be seen, the prosthetic of embodiments may be balanced along a central vertical axis, with symmetry of the prosthetic being present on each side of the vertical axis. The center axis is labelled 965. Symmetry may exist along other reference axes of embodiments as well. For example, symmetry along various reference axes may exist on either side of the split of some embodiments.

Figure 10:
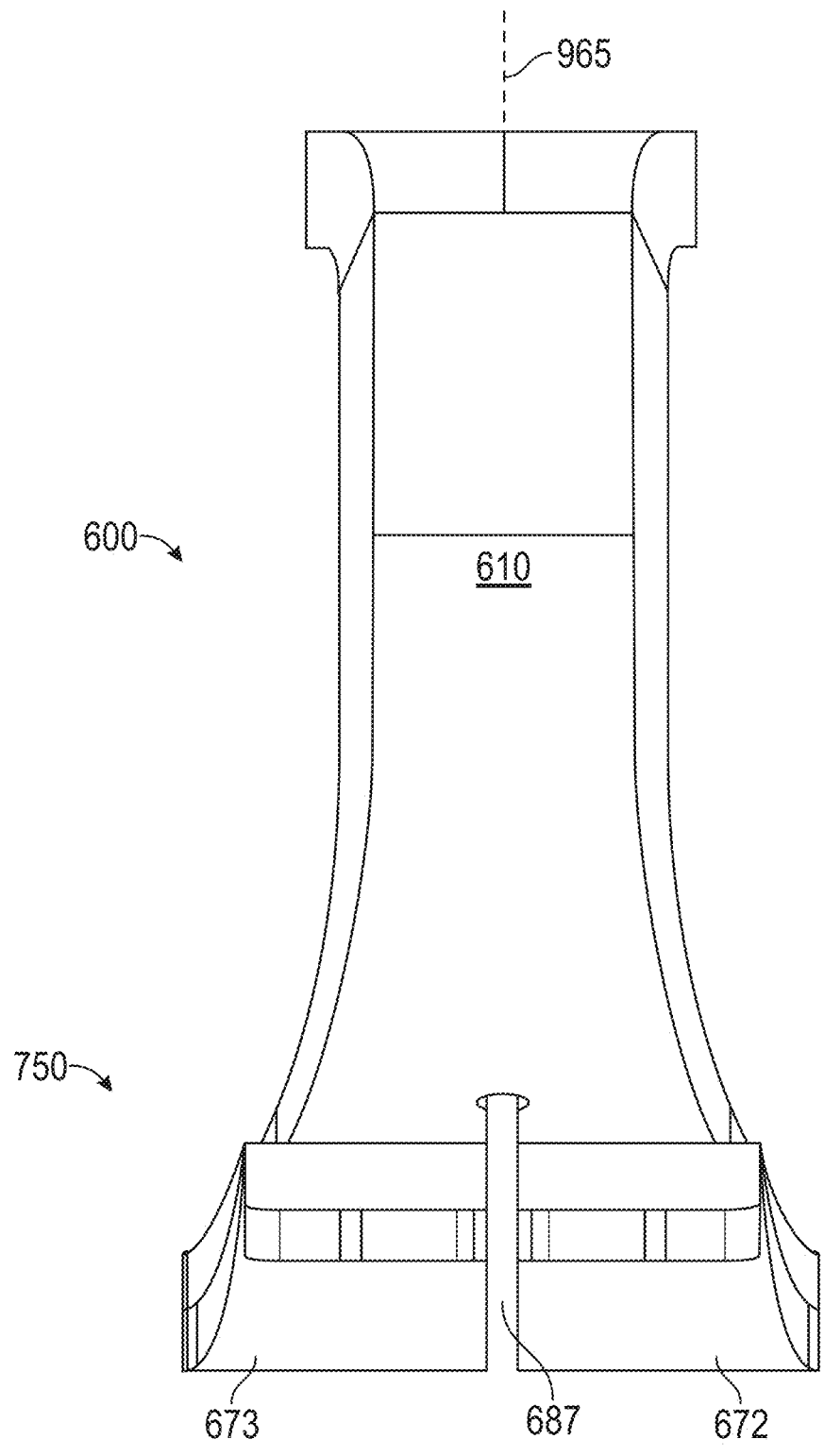
FIG. 10 shows a rear upright view of the prosthetic foot of FIG. 6, with J-shaped keel, and split sole plate, as may be employed in some embodiments.

FIG. 10 shows a rear upright view of the prosthetic foot of FIG. 6, with J-shaped keel 610, passages with composite rivets, and sole plates 672, 673, with split 687 between them as may be employed in some embodiments. The location of the underside of the sole plates and the split heel region 750 are visible in this view. As can be seen in FIG. 10 as well, the prosthetic of embodiments may be balanced along a central vertical axis 965, with symmetry of the prosthetic being present on each side of the vertical axis. FIG. 10 also provides that embodiments may have prosthetics with split lateral and medial sides for an entire length of the heel or the sole plate, in each case without intervening connection portions (see split 985 without intervening connecting portions between the two sole plates 672 and 673).

Figure 11:
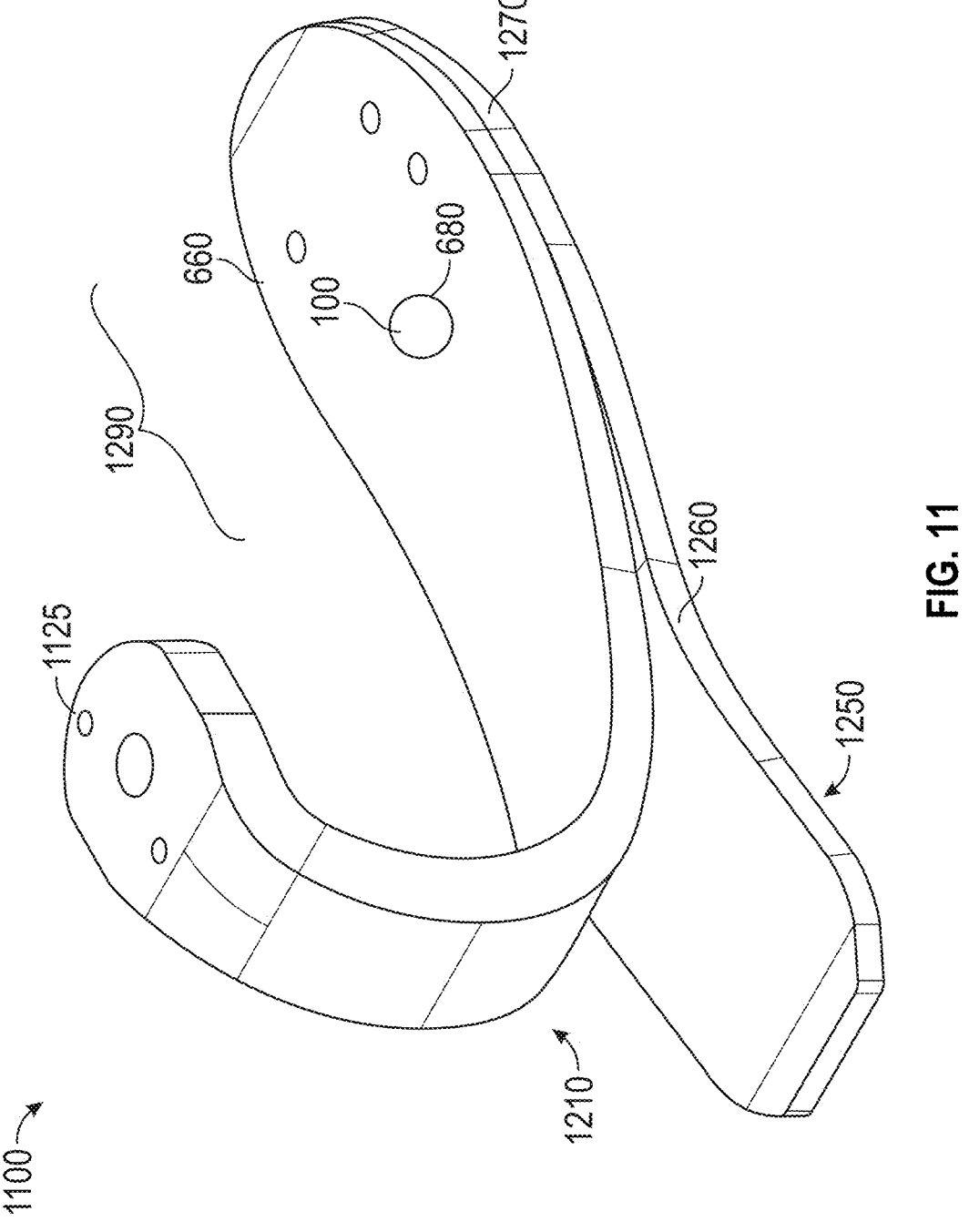
FIG. 11 shows a rear perspective view of a prosthetic foot without split keel and sole plate as may be employed in some embodiments.

FIG. 11 shows a rear perspective view of a prosthetic foot 1100 with J-shaped keel 1210, sole plate 1260, and composite rivet passage 680 with rivet 100 as may be employed in embodiments. The composite rivet passage 680 for a composite rivet to secure spring layers, along with various regions and components are shown in FIG. 11. As can be seen in FIG. 11 the sole plate 1260 and the keel 1210 are attached in the keel-toe region 660 via a composite rivet 100. The composite rivet 100 is shown between the edges of the sole plate and keel and in the first third of the prosthetic. A single or multiple composite rivets may be located in other areas of the prosthetic as well. Such composite rivets may be positioned and installed so as to secure a keel to a sole plate or other components of a prosthetic or an orthotic. The size and shape of the passage in which the composite rivet is inserted can add to the strength of the connection created by the composite rivet. The configuration of the composite rivet may add to the strength of the connection created by the composite rivet. Also labelled in FIG. 11 are the sole-plate keel attachment region 1290, sole plate toc region 1270, heel 1250, and upper cantilevered portion 1125.

Figure 12:
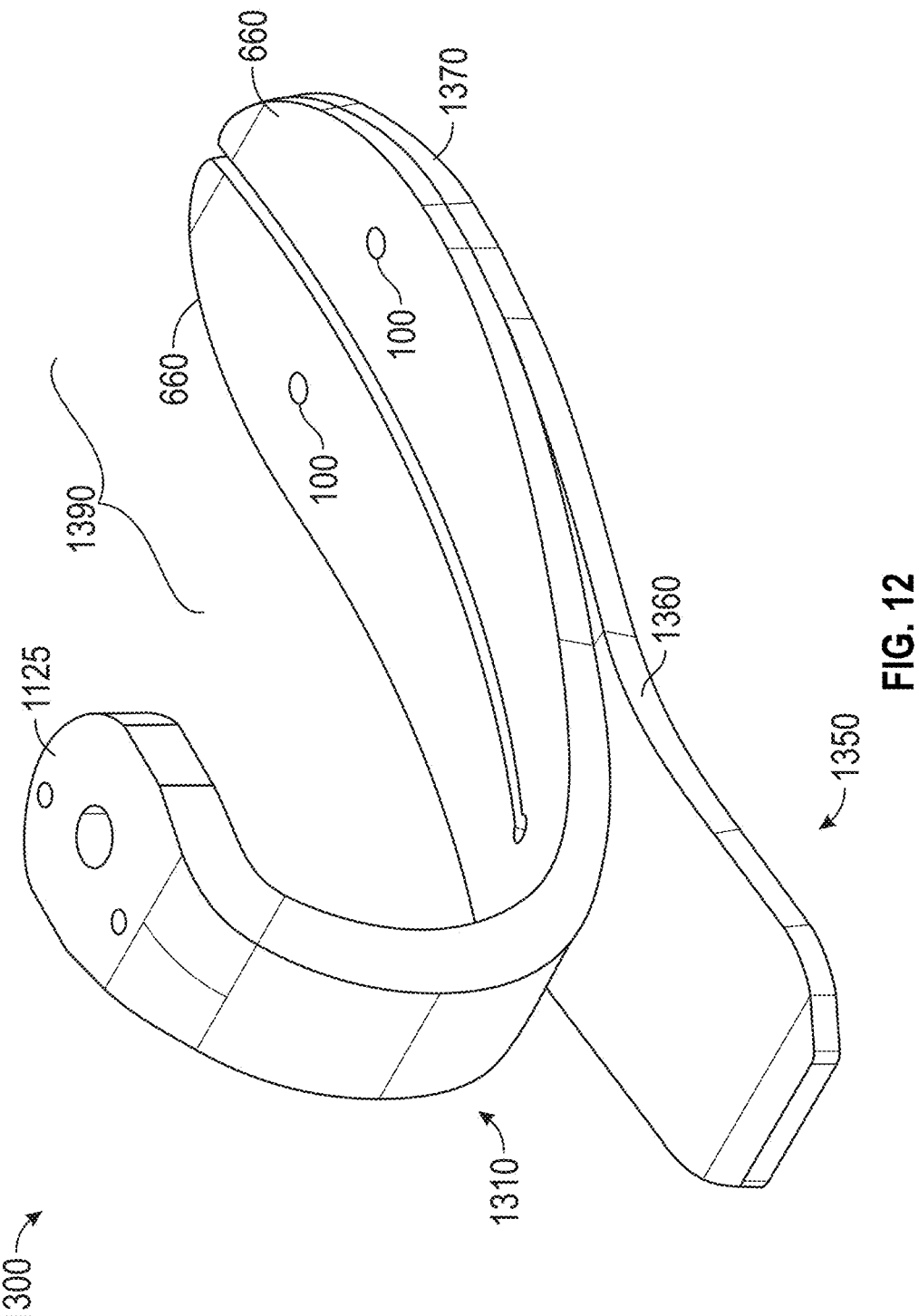
FIG. 12 shows a rear perspective view of a prosthetic foot with partial split keel and sole plate, each providing spring plate functionality, as may be employed in some embodiments.

FIG. 12 shows a rear perspective view of a prosthetic foot 1300 with partial split keel 1310 and split sole plate 1360, each providing spring plate functionality, as may be employed in some embodiments. Composite rivets 100 along with various regions and components are labelled in FIG. 12. These include sole plate 1360, heel 1350, sole plate toe region 1370, keel-toe region 660, sole plate-keel attachment region 1390, and upper cantilevered portion 1125. As can be seen in FIG. 12 the split sole plate and the split J-shaped keel are attached in the keel-toe region 660 via a pair of composite rivets 100. The composite rivets 100 are shown between the edges of the sole plate and the keel and in the first third of the prosthetic. Various composite rivets, composite rivet locations, and composite rivet materials may be employed in this and other embodiments.

Figure 13:
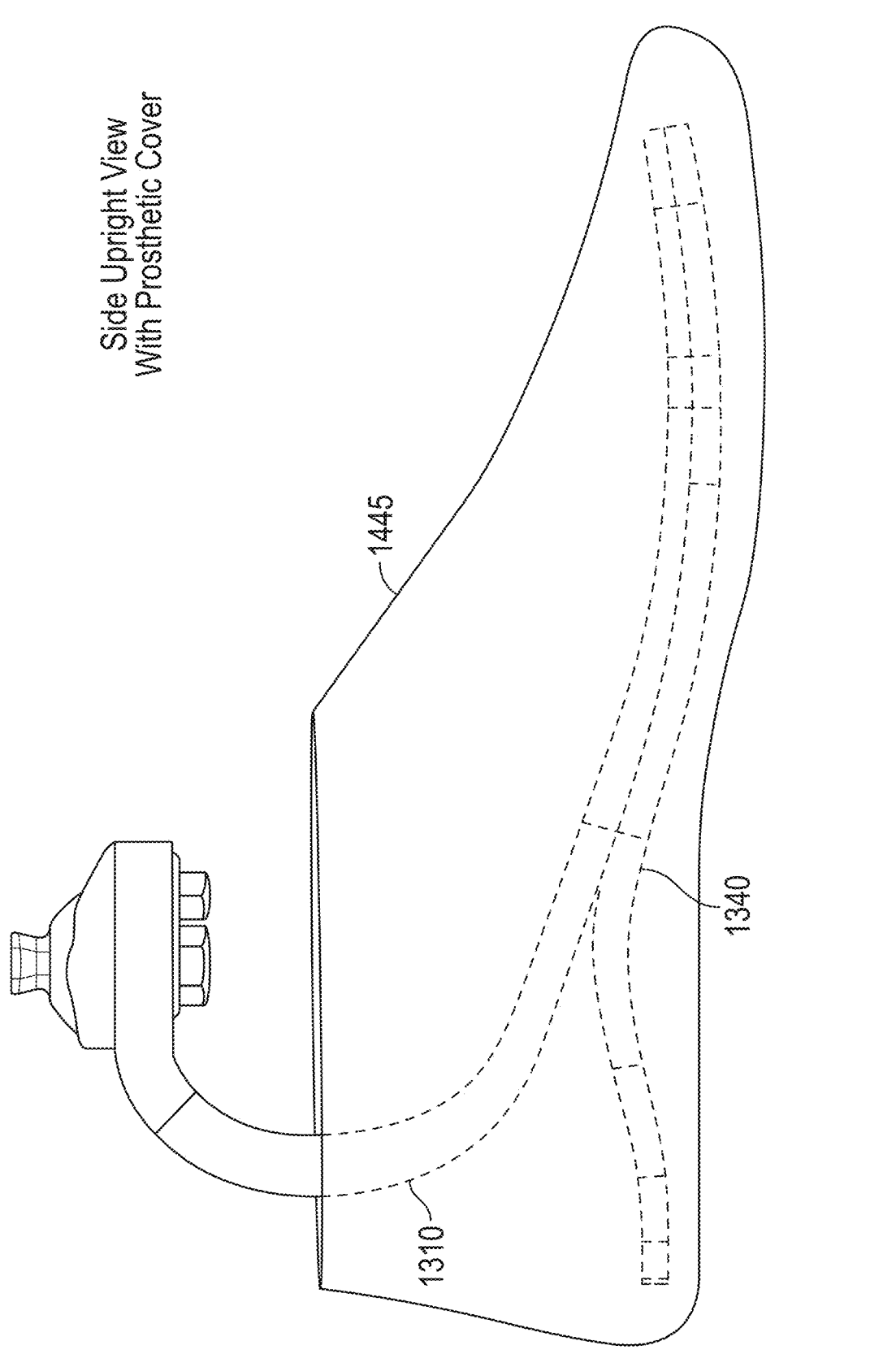
FIG. 13 shows a side, upright view, of the prosthetic foot of FIG. 13 with split J-shaped keel, sole plate, and prosthetic cover as may be employed in some embodiments.

FIG. 13 shows a side, upright view, of the prosthetic foot of FIG. 12 with split J-shaped keel 1310, split sole plate 1340, and prosthetic cover 1445 as may be employed in embodiments. The prosthetic cover 1445 is shown having a somewhat anatomic foot configuration although other configurations may also be employed in embodiments. Covers may be employed with various features including additional surface friction, sound management, and for other reasons as well. Keels of embodiments may be a solid plate or be split in the forefoot area in some embodiments.

Figure 14:
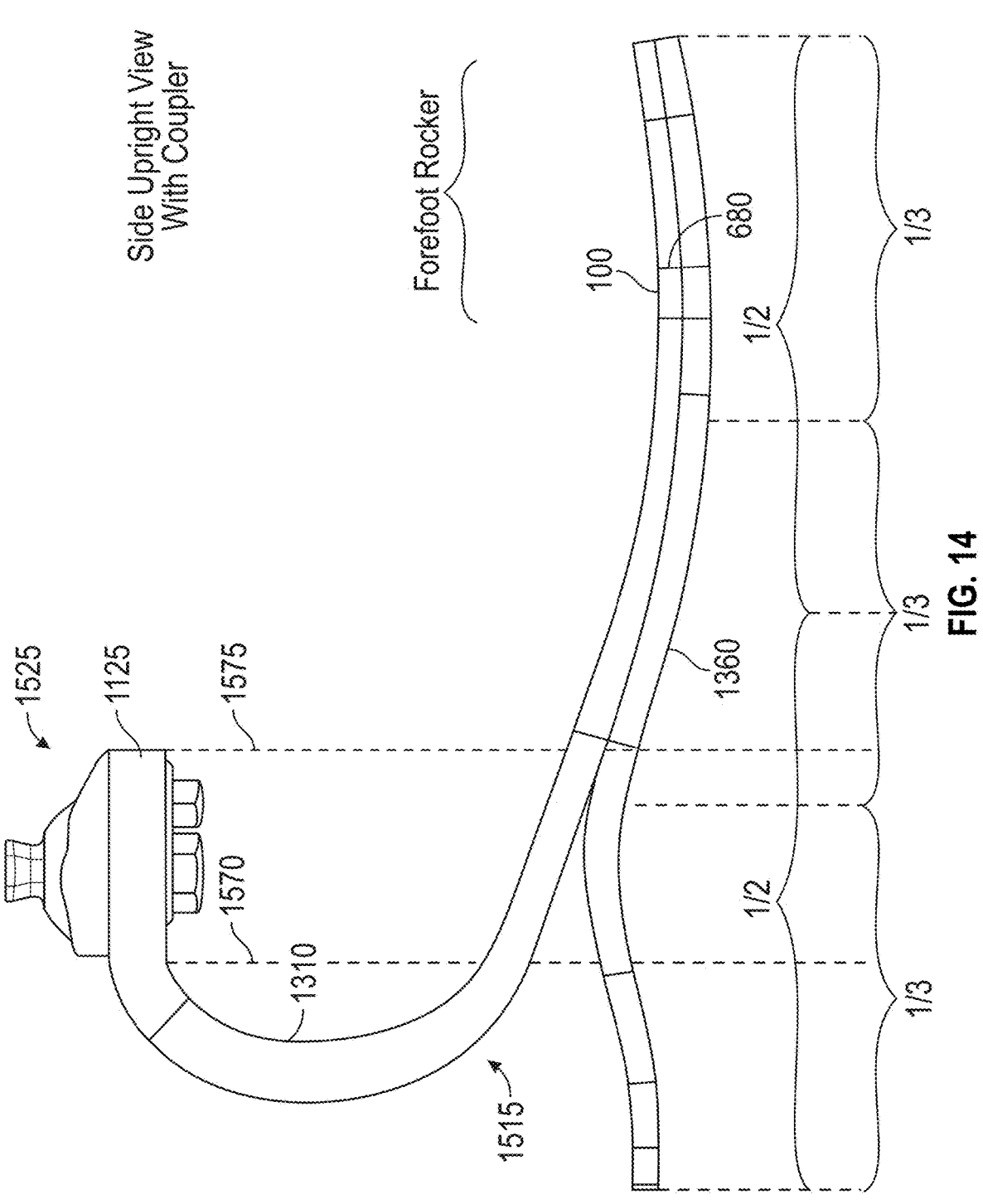
FIG. 14 shows a side, upright view of the prosthetic foot of FIG. 13 with split J-shaped keel, sole plate, composite rivets, and metallic pyramid coupler, as may be employed in some embodiments.

FIG. 14 shows a side, upright view of the prosthetic foot of FIG. 12 with split J-shaped keel 1310, split sole plate 1360, composite rivet passages 680, composite rivet 100, posterior section of keel 1515, and metallic pyramid coupler 1525, as may be employed in some embodiments. Various coupler configurations and placements may be employed in embodiments. In FIG. 14, the coupler is shown in a cantilevered region 1125 of the J-shaped keel and in the cross-section of the keel having the greatest thickness. The tapering nature of the cross section of the J-shaped keel is also visible in FIGS. 14 and 17. A reference scale is provided at the bottom of FIG. 14 and reference lines 1570, 1575, show relative position versus the scale provided in FIG. 14. Single group of layers or multiple groups of layers may be employed as sole plates in embodiments. Likewise, the keel may be a single group of layers or multiple groups of layers embodiments. Each plate may have a split at least in the toe region of the prosthetic in some embodiments. In some embodiments, as shown above, the bottom may comprise sole plates with a split between them while in others the sole plate and/or keel may not be split. The keel may be split along a majority of its length as well.

Figure 15:
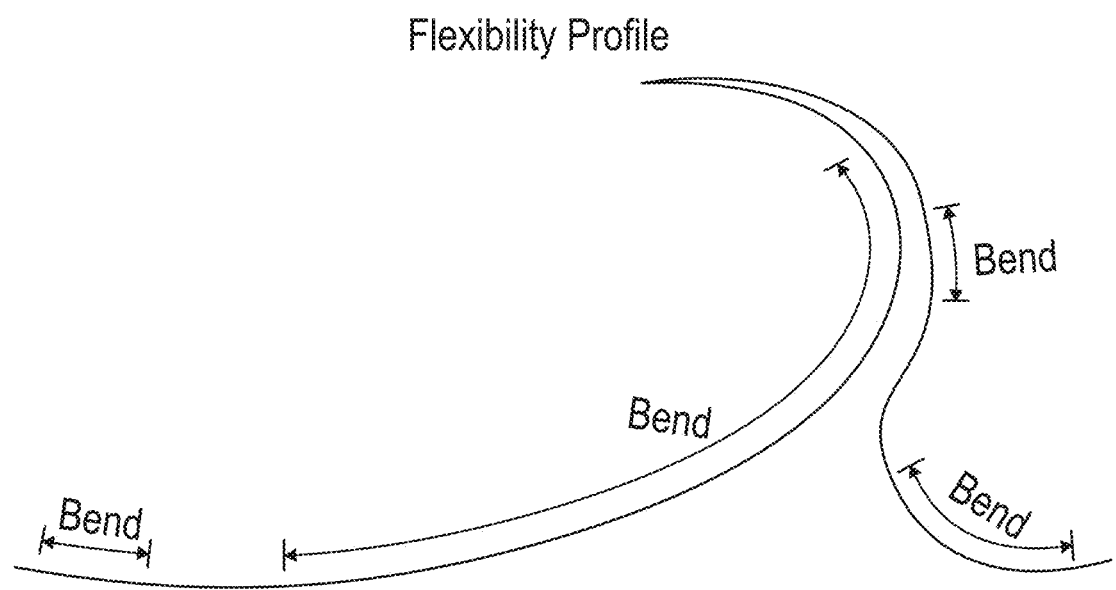
FIG. 15 shows an exemplary flexibility/rigidity profile for a prosthetic foot with J-shaped keel, as may be employed in some embodiments.

FIG. 15 shows an exemplary flexibility/rigidity profile for a prosthetic foot with J-shaped keel, as may be employed in some embodiments. The various sections labelled bend identify lengths along the keel or sole plates or both that may be flexible or flex in a substantially cohesive way. In other words, their relative stiffnesses or flexibility may differ but they may function in a cohesive manner or substantially cohesive manner.

Figure 16:
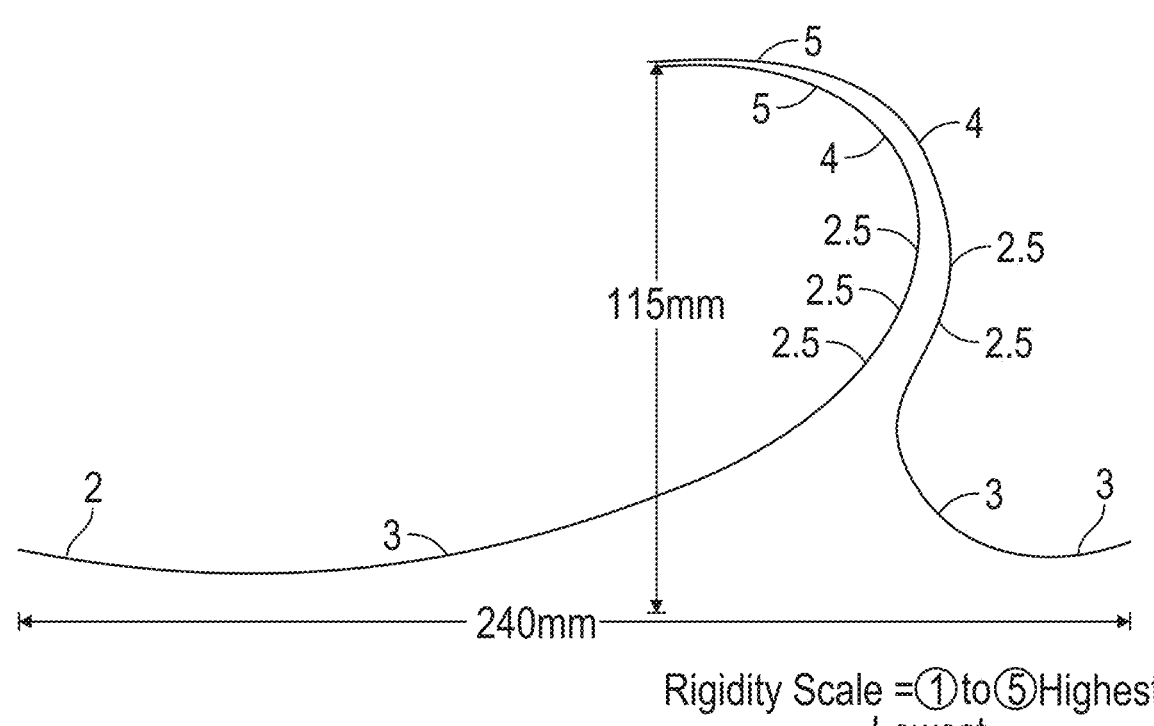
FIG. 16 shows an exemplary flexibility/rigidity profile for a prosthetic foot with J-shaped keel, as may be employed in some embodiments.

Annotated FIG. 16 shows an exemplary schematic flexibility profile for a prosthetic foot with J-shaped keel as may be employed in embodiments. The various labelled sections identify lengths along the keel or sole plates or both that may be flexible or flex in a substantially cohesive way and with a relativity scale regarding this flexibility as well. FIG. 16 includes a numeric scale to show relative rigidity (or flexibility) between the different portions of the prosthetic of FIGS. 15 and 16. Other portions of the prosthetic foot may be more or less flexible as well. Flexibility may be adjusted by adding or removing layers of fiber or modifying layers of fiber, for example changing a UD fiber layer to bi-directional fiber layer.

Figure 17:
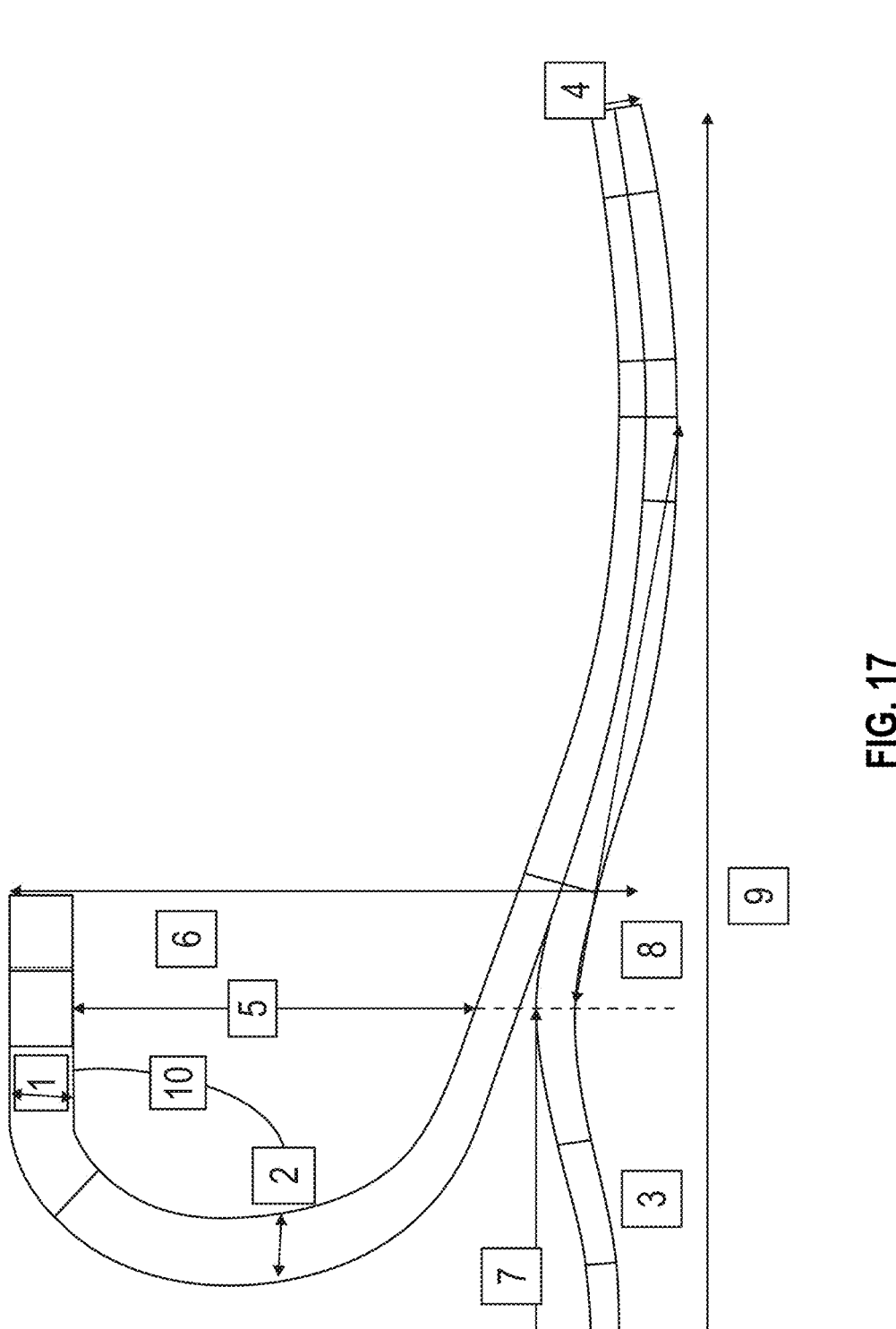
FIG. 17 shows exemplary measurement points corresponding with Table 1 for a certain size prosthetic foot with split j-shaped keel, sole plate, and composite rivets, as may be employed in some embodiments.

FIG. 17 shows exemplary measurement points corresponding with Table 1 for a certain size prosthetic foot with split J-shaped keel and split sole plate, as may be employed in embodiments. The dimensions of FIG. 17 and Table 1 are directed to a certain size and may be modified for other sizes, as well as modified for other reasons in embodiments. Certain dimensional ratios may be held consistently across same-sized embodiments and certain dimensional ratios may vary across same-sized embodiments.

FIGS. 18A-18D show forces that may be present or developed around composite rivets and components secured by a composite rivet in some embodiments. Forces may be transferred between the rivet/layer interface 2025 as well as the rivet component interface 2026. These forces may include static and dynamic forces and may be transferred through friction or other transfer mechanisms. Composite rivets may assert inward axial compressive forces to components or layers being secured together and may impose frictional surface forces along a rivet surface interface. These frictional forces and compressive forces may act to hold layers or other components together. These forces may also resist rotation of layers or components being secured by a composite rivet 100. Axial forces are labelled 2050.

Figure 18A:
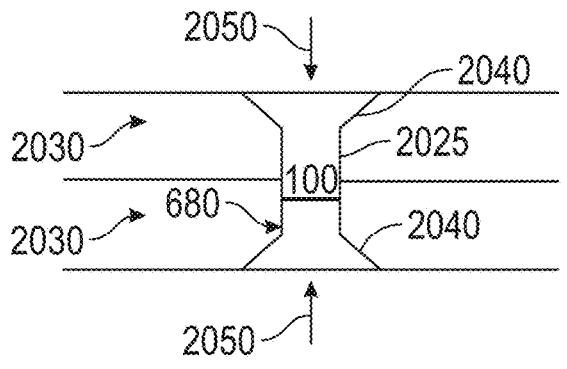
FIGS. 18A-18D show forces that may be present or developed around composite rivets and components secured by a composite rivet as may be employed in some embodiments.
Figure 18B:
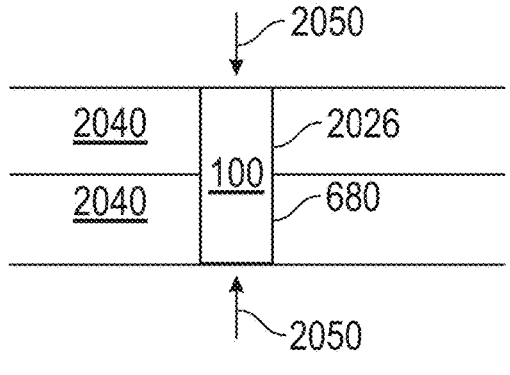

In embodiments, multiple composite rivets may be employed to provide greater resistance to torsion or to provide greater securement forces. The positioning of the composite rivets may also be selected to provide targeted securement forces or movement deterrence. Exemplary shapes of the rivet 100 and the passages 680 for the rivet 100 are present in FIGS. 18A and 18B and may be selected to develop different frictional or compressive forces for a particular expected loading. For example, as shown in FIG. 18A, a chamfered top and bottom with chamfered edges 2040 of a composite rivet 100 may be employed to develop greater compressive forces than what may be developed by a purely cylindrical rivet without chamfered or other non-vertical sides.

Figure 18C:
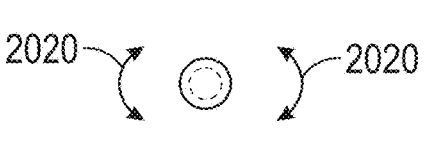
Figure 18D:
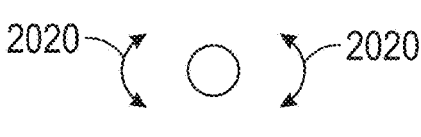

FIGS. 18C and 18D show rotational forces 2020 that may be opposed by composite rivets of embodiments. Opposition of these rotational forces may serve to keep layers or other components being secured from rotating differently from each other. In other words, the secured layers 2030 or components 2040 may stay aligned or close to aligned to each other in some embodiments. These rotational forces may be opposed by compressive forces developed by the rivets as well as surface friction between the rivets and the components being secured.

Figure 19:
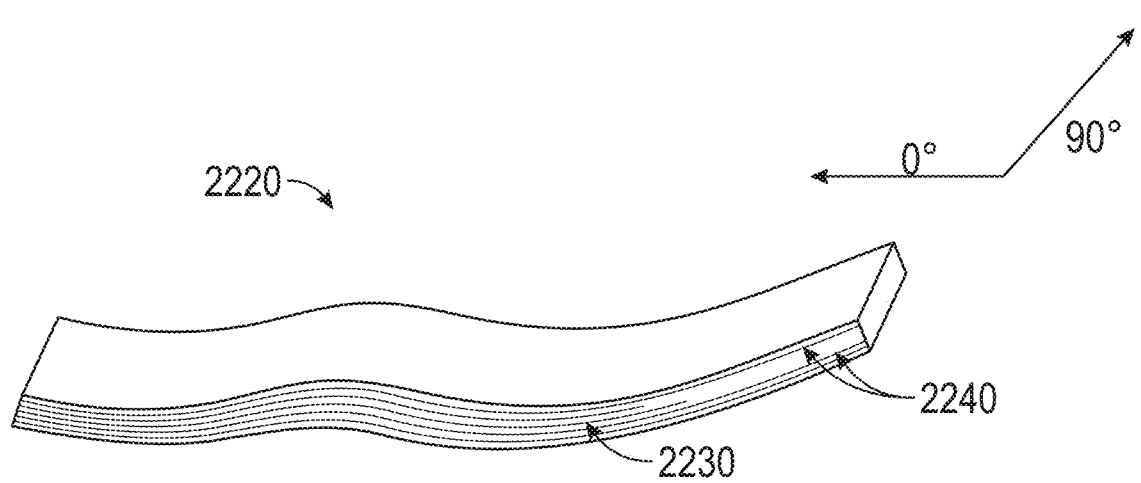
FIG. 19 shows a sole plate layup as may be employed in some embodiments.

FIG. 19 shows sole plate 2220 layups as may be employed in some embodiments. Sole plates of some embodiments may employ composite fiber fabric, bidirectional layers (carbon fiber, aramid fiber, glass fiber, etc.) e.g., ±45°±30°, etc., 0° Unidirectional Full Length (carbon fiber, aramid fiber, glass fiber, etc.), 0° Ply drop-off (carbon fiber, aramid fiber, glass fiber, etc.), 90° Unidirectional full length and/or ply drop-off (carbon fiber, aramid fiber, glass fiber, etc.). As described above, the layup layers may have different lengths and may drop off 2230 as is shown in FIG. 19. As the layers drop off the flexibility of the sole plate or other component increases and the thickness decreases as fewer layers are present. Some full-length sections 2240 may be present along the entire length of the sole plate 2220 or other component. These full-length sections 2240 may comprise one or more layers and may positioned at outer surfaces of the sole plate 2220 as well as internal positions of the sole plate 2220 along it length. The direction of the fiber may be 0° and 90° as well as other orientations. A reference axis is shown at FIG. 19.

Figure 20:
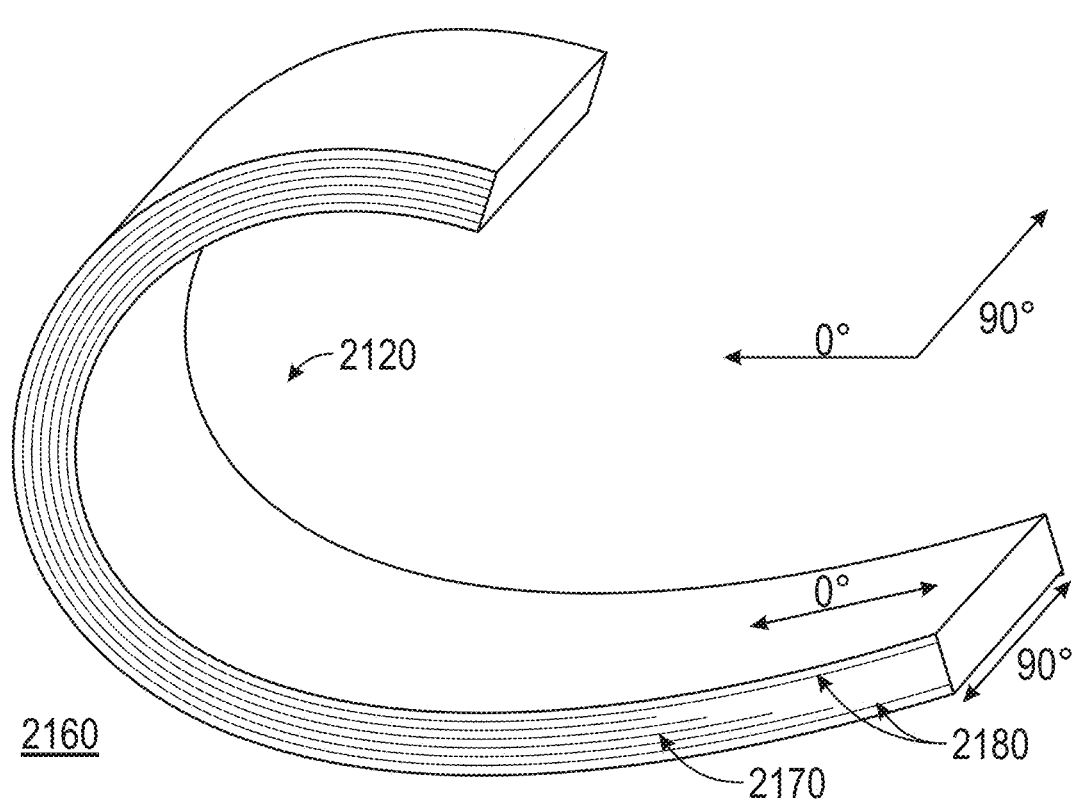
FIG. 20 shows a keel layup as may be employed in some embodiments.

FIG. 20 shows keel 2120 layups as may be employed in embodiments. Keel 2120 layups of embodiments may employ composite fiber fabric, bidirectional layers (carbon fiber, aramid fiber, glass fiber, etc.) e.g., ±45°±30°, etc., 0°

Unidirectional full length (carbon fiber, aramid fiber, glass fiber, etc.), 0° Unidirectional ply-drop off (carbon fiber, aramid fiber, glass fiber, etc.), 90° Unidirectional full length and/or ply drop-off (carbon fiber, aramid fiber, glass fiber, etc.). The layup layers may have different lengths and may drop off 2170 as is shown in FIG. 20. As the layers drop off the flexibility of the keel or other component increases and the thickness decreases as fewer layers are present. Some full-length sections 2180 may be present along the entire length of the keel 2120 or other component. These full-length sections 2180 may comprise one or more layers and may positioned at outer surfaces of the keel as well as internal positions of the keel 2120 along its length. The direction of the fiber is shown by the 0° and 90° arrows as well as by the reference axis.

Keel and sole plate lay-ups of embodiments may be adapted for size. For example, an increase or decrease in the number of layers of full-length and/or ply drop-off layers sections may be employed. Layups of embodiments may be adapted for weight or activity level as well. For example, an increase or decrease in the number of layers of full-length and/or ply drop-off layer sections may be employed. Keel and sole plate lay-ups may also employ other fibers such as fiberglass and other composite layered materials.

TABLE 1

Non-Limiting Exemplary Dimensions Corresponding to an Exemplary size 27 P5 foot - as shown in FIG. 17. Other dimensions in embodiments may also be employed.

| Number | Description | Measurement [mm] |
|---|---|---|
| 1 | Thickness of composite at mount | 10.9 |
| 2 | Thickness of composite at apex of "J" curve | 11.3 |
| 3 | Thickness of sole plate at 20% length from heel | 5.4 |
| 4 | Thickness of composite at toe tip | 9.8 |
| 5 | Inside width of keel | 70.6 |
| 6 | Overall height of foot | 111 (excluding pyramid) |
| 7 | Length of heel portion of sole plate | 67 (measured to the pyramid hole center axis) |
| 8 | Sole plate length from apex of posterior curve to apex of toe curve | 104 |
| 9 | Overall length of (foot) soleplate | 235 |
| 10 | The curve may use more than a single radius. The outside curve can be described by an Ellipse with a major radius of 39.5 and a minor radius of 29.3. | Ellipse Major radius 41 Minor radius 29 |

While various features, combinations of features, and embodiments are provided herein, other features, combinations of features, and embodiments may also be employed. Features may be combined across embodiments and with different embodiments while remaining within the teachings of the disclosure. For example, split keel and split sole plates as well as intact keels and intact sole plates are shown herein. Other embodiments may include multiple keel elements and/or multiple sole plates. Still further keel and sole plate designs may be employed in embodiments. Composite rivets of carbon, glass, and aramid fibers are mentioned above but still further materials may be employed in composite rivets of embodiments.

What is claimed is:

1. A composite prosthetic foot comprising:

a composite keel spring comprising an upper portion and a lower portion, the lower portion having a keel-toe region;

a composite sole plate spring positioned below the composite keel spring and coupled to the composite keel spring in the keel-toe region; and a composite rivet positioned in the keel-toe region and configured to attach the composite sole plate speing to the composite keel spring in the keel-toe region, wherein the composite rivet comprises a layer of thermoset carbon fiber composite material, the layer of thermoset carbon fiber composite material of the rivet having been twisted via torsional rotation of the layer of thermoset carbon fiber composite material.

2. The prosthetic foot of claim 1 wherein the composite rivet is positioned in the composite keel spring and the composite sole plate spring, and wherein the layer of thermoset carbon fiber composite material comprises at least one of a unidirectional carbon fiber sheet or a multidirectional carbon fiber sheet.

3. The prosthetic foot of claim 1 wherein the composite sole plate spring comprises a heel.

4. The prosthetic foot of claim 1 wherein the composite rivet is positioned in the composite keel spring and the composite sole plate spring and wherein the upper portion has a portion extending forward in the direction of the keel-toe region.

5. The prosthetic foot of claim 1 wherein the composite rivet is positioned in a first hole, the first hole positioned in the composite sole plate spring and in the composite keel spring in the keel-toe region, the keel-toe region located anterior to a widest portion of the composite sole plate spring.

6. The prosthetic foot of claim 5 wherein the composite rivet is symmetrically formed and wherein the first hole has an opening wider than an inner passage of the first hole.

7. The prosthetic foot of claim 1 wherein the composite rivet extends into the composite keel spring and into the composite sole plate spring and an upper end of the composite rivet lies flush with an outer surface of the composite keel spring or the upper end of the composite rivet is recessed when compared with the outer surface of the composite keel spring.

8. The prosthetic foot of claim 1 wherein the composite rivet comprises one or more of the following: dry or prepreg: UD (UniDirectional) fiber, rolled UD (UniDirectional) fiber bunches, weaved fiber stockings, UD (UniDirectional) fiber bunches, twisted UD (UniDirectional) fiber bunches, twisted fibers, or roped out fibers.

9. The prosthetic foot of claim 1 wherein the composite keel spring is formed as a J-shaped or L-shaped keel and, wherein the composite rivet is positioned in an anterior third of the composite sole plate spring, the anterior third of the composite sole plate spring having a surface that is upwardly sloping and curved.

10. A composite prosthetic foot comprising:

a first composite spring layer, the first spring layer comprising an upper portion and a lower portion; and a second composite spring layer coupled to the first spring layer, wherein the first spring layer is coupled to the second spring layer with a twisted carbon fiber rivet, the rivet comprising a first layer of unidirectional fiber sheet or multidirectional fiber sheet or both, the first layer having a twist present in it, the twist of the first layer imparted by the first layer having been twisted via torsional rotation of the first layer, wherein the second spring layer is a sole plate.

11. The composite prosthetic foot of claim 10 wherein the sole plate is coupled to the first spring layer in an anterior portion of the sole plate and wherein the upper portion has a portion extending forward in the direction of a keel-toe region.

12. The composite prosthetic foot of claim 10 wherein the rivet comprises the twist of the first layer imparted by the first layer having been twisted via torsional rotation of the first layer is twisted about a longitudinal reference line of the rivet.

13. A composite prosthetic foot comprising:

a composite J-shaped keel, the keel comprising a split pronged lower portion;

a composite first sole plate coupled to a first prong of the split pronged lower portion, the first sole plate having a continuous exterior bottom surface with a length extending in the first prong from a heel region of the composite prosthetic foot to a first anterior distal end of the composite prosthetic foot; and a composite second sole plate coupled to a second prong of the split pronged lower portion, the second sole plate having a continuous exterior bottom surface with a length extending in the second prong from the heel region of the composite prosthetic foot to a second anterior distal end of the composite prosthetic foot;

wherein the first sole plate is spaced apart from the second sole plate along an entire side across from the second sole plate, and wherein the first sole plate is coupled to the first prong of the split pronged lower portion with a first twisted carbon fiber rivet, the first twisted carbon fiber rivet having been twisted via torsional rotation of the first twisted carbon fiber rivet.

14. The prosthetic foot of claim 13 wherein the J-shaped keel and the first and second sole plates comprise one of more layers of carbon fiber.

15. The prosthetic foot of claim 13 wherein the first sole plate is coupled to the first prong of the split pronged lower portion in an anterior third of the first prong, the anterior third sloping upwards towards the first anterior distal end of the composite prosthetic foot.

16. The prosthetic foot of claim 13 wherein the first sole plate is coupled to the first prong of the split pronged lower portion with at least two carbon fiber rivets.

17. The prosthetic foot of claim 13 wherein the keel comprises an upper portion having a portion extending forward in the direction of a keel-toe region.

18. The prosthetic foot of claim 17 wherein the first sole plate is coupled to the second prong of the split pronged lower portion with a second twisted carbon fiber rivet, the second twisted carbon fiber rivet having been twisted via torsional rotation of the second twisted carbon fiber rivet.

19. The prosthetic foot of claim 13 wherein the first sole plate is coupled to the first prong of the split pronged lower portion with the first twisted carbon fiber rivet positioned in an anterior forward third region of the first sole plate, the anterior forward third region of the first sole plate sloping upwardly towards a distal end of the anterior forward third region of the first sole plate.

20. A composite prosthetic foot comprising:

a first composite spring layer, the first spring layer comprising an upper portion and a lower portion; and a second composite spring layer coupled to the first spring layer, wherein the first spring layer is coupled to the second spring layer with a twisted carbon fiber rivet, the rivet comprising a first layer of unidirectional fiber or multidirectional fiber or both, the first layer having a twist present in it, the twist of the first layer imparted by the first layer having been rotationally twisted about a longitudinal reference line of the rivet, wherein the second spring layer is a sole plate.

21. The composite prosthetic foot of claim 20 wherein the twisted carbon fiber rivet is positioned in an anterior portion of the composite prosthetic foot, the anterior portion solely located in a forward third of the composite prosthetic foot, and wherein the composite prosthetic foot comprises carbon fibers.

* * * * *